US010826118B2

United States Patent
Iojoiu et al.

(10) Patent No.: US 10,826,118 B2
(45) Date of Patent: Nov. 3, 2020

(54) PROCESS FOR PREPARING UNIPOLAR CATION-CONDUCTING IONOMERS FROM DIFLUORO IONIC MONOMERS

(71) Applicants: CENTRE NATIONAL DE LA RECHERCHE SCIENTIFIQUE, Paris (FR); INSTITUT POLYTECHNIQUE DE GRENOBLE, Grenoble (FR)

(72) Inventors: Cristina Iojoiu, Vourey (FR); Amadou Thiam, Amiens (FR); Olesia Danyliv, Mölndal (SE); Régis Mercier, Irigny (FR); Jean-Yves Sanchez, Saint-Ismier (FR)

(73) Assignees: CENTRE NATIONAL DE LA RECHERCHE SCIENTIFIQUE, Paris (FR); INSTITUT POLYTECHNIQUE DE GRENOBLE, Grenoble (FR)

( * ) Notice: Subject to any disclaimer, the term of this patent is extended or adjusted under 35 U.S.C. 154(b) by 60 days.

(21) Appl. No.: 15/746,126

(22) PCT Filed: Jul. 21, 2016

(86) PCT No.: PCT/FR2016/051905
§ 371 (c)(1),
(2) Date: Jan. 19, 2018

(87) PCT Pub. No.: WO2017/013375
PCT Pub. Date: Jan. 26, 2017

(65) Prior Publication Data
US 2018/0212274 A1    Jul. 26, 2018

(30) Foreign Application Priority Data

Jul. 22, 2015 (FR) ..................................... 15 56967

(51) Int. Cl.
*H01M 10/0565* (2010.01)
*C08G 65/40* (2006.01)
(Continued)

(52) U.S. Cl.
CPC ....... *H01M 10/0565* (2013.01); *C07C 303/22* (2013.01); *C07C 303/40* (2013.01);
(Continued)

(58) Field of Classification Search
CPC ...... C08L 65/00; C08L 2666/04; C08L 27/12; C08L 79/04; C08L 79/02; C08L 2666/02; C08L 2666/06; C08L 2666/22; C08L 81/00; C08L 41/00; C08L 2666/36; C08L 101/12; C08L 25/18; C08L 27/18; C08L 81/08; C08L 23/26; C08L 25/08; C08L 27/00; C08L 73/02; C08L 2203/20; C08L 2205/02; C08L 71/02; C08L 87/005; H01B 1/127; H01B 1/122; H01B 1/128; H01B 1/06; H01B 1/12; H01B 1/20; H01B 51/0037; H01B 51/5088; H01B 2251/5369; H01B 51/0035; H01B 51/0021; H01B 51/0541; H01B 51/5206; H01B 51/0036; H01B 51/0048; H01B 2251/305; H01B 2251/306; H01B 2251/564; H01B 51/0039; H01B 51/004; H01B 51/0043; H01B 51/442; H01B 51/0052; H01B 51/50; H01B 51/52; C09D 179/02; C09D 165/00; C09D 11/36; Y02E 10/549; Y02E 60/13; Y02E 60/366; B82Y 30/00; B82Y 10/00; B82Y 20/00; B82Y 5/00; C08G 61/126; C08G 61/124; C08G 73/0266; C08G 2261/126; C08G 2261/1426; C08G 2261/143; C08G 2261/148; C08G 2261/149; C08G 2261/3324; C08G 2261/3325; C08G 2261/418; C08G 2261/516; C08G 2261/792; C08G 61/02; C08G 61/08; C08G 65/4006; C08G 65/4031; C08G 65/48; C08G 73/18; C08G 81/00; C08G 18/4009; C08G 18/4804; C08G 18/46816; C08G 18/4837; C08G 2101/0025; C08G 2101/005; C08G 18/48; C08G 2105/02; H01G 11/48; H01G 11/56; H01G 9/04; C09J 165/00; Y10S 428/917; Y10S 977/783; Y10S 977/784; Y10S 977/788; Y10S 521/902; Y10S 521/914; H01M 2008/1095; H01M 2300/0082;
(Continued)

(56) References Cited

U.S. PATENT DOCUMENTS

2008/0114183 A1   5/2008   Moore et al.
2009/0163692 A1   6/2009   Moore et al.
2015/0218313 A1   8/2015   Wang et al.

FOREIGN PATENT DOCUMENTS

WO    00/77057    12/2000

OTHER PUBLICATIONS

Kui Xu et al: "Highly Conductive Aromatic Ionomers with Perfluorosulfonic Acid Side Chains for Elevated Temperature Fuel Cells", Macromolecules, vol. 44, No. 12, Jun. 28, 11.
(Continued)

*Primary Examiner* — Deborah K Ware
(74) *Attorney, Agent, or Firm* — Ostrolenk Faber LLP

(57) ABSTRACT

The invention relates to a process for preparing unipolar cation-conducting ionomers from fluoro ionic monomers, to said unipolar cation-conducting ionomers, to the uses thereof, to an electrolytic composition comprising at least one of said unipolar cation-conducting ionomers and to an electrochemical device comprising at least one of said unipolar cation-conducting ionomers, especially as electrolyte.

22 Claims, 2 Drawing Sheets

(51) Int. Cl.
| | |
|---|---|
| *H01M 10/052* | (2010.01) |
| *C08G 65/48* | (2006.01) |
| *C07C 303/22* | (2006.01) |
| *C07C 303/40* | (2006.01) |
| *C07C 309/24* | (2006.01) |
| *C07C 311/09* | (2006.01) |
| *C07C 315/02* | (2006.01) |
| *C07C 317/22* | (2006.01) |
| *C07C 319/14* | (2006.01) |
| *C07C 323/66* | (2006.01) |
| *C08L 71/02* | (2006.01) |
| *H01M 10/0525* | (2010.01) |

(52) U.S. Cl.
CPC .......... *C07C 309/24* (2013.01); *C07C 311/09* (2013.01); *C07C 315/02* (2013.01); *C07C 317/22* (2013.01); *C07C 319/14* (2013.01); *C07C 323/66* (2013.01); *C08G 65/4006* (2013.01); *C08G 65/4031* (2013.01); *C08G 65/48* (2013.01); *C08L 71/02* (2013.01); *H01M 10/052* (2013.01); *H01M 10/0525* (2013.01); *C08L 2203/20* (2013.01); *H01M 2300/0028* (2013.01)

(58) Field of Classification Search
CPC .. H01M 8/1004; H01M 8/103; H01M 8/1067; H01M 10/0525; H01M 10/0565; H01M 4/86; H01M 4/92; H01M 8/10; H01M 8/1027; H01M 8/1032; H01M 8/1039; H01M 8/1044; H01M 10/052; H01M 14/005; H01M 2300/0028; H01M 2300/0088; H01M 4/8605; H01M 4/8668; H01M 4/90; H01M 4/9075; H01M 4/921; H01M 4/925; H01M 4/926; H01M 4/928; H01M 4/96; H01M 8/04089; H01M 8/04228; H01M 8/04291; H01M 8/04303; H01M 8/04701; H01M 8/1009; H01M 8/1023; H01M 8/1025; H01M 8/1034; H01M 8/1048; H01M 8/1086; H01M 8/1088; H01M 2300/0085; H01M 4/366; H01M 4/505; H01M 4/525; H01M 4/587; H01M 6/164; C08F 14/18; C08F 214/26; C08F 214/262; C08F 2/00; Y02P 70/56; C07D 233/64; C07D 263/32; C07D 491/048; C08K 5/0091; C08K 2201/011; C08K 3/01; C09B 11/02; C09B 11/24; C09B 17/00; C09B 19/00; C09B 1/00; C09B 21/00; C09B 23/0091; C09B 23/14; C09B 57/00; C09B 5/14; C09K 11/06; C09K 2211/1007; C09K 2211/1033; C09K 2211/1037; C09K 2211/1044; C09K 2211/1441; C09K 9/02; G02F 1/1503; G02F 1/1506; G02F 1/155; G02F 1/161; G02F 1/163; G02F 2001/1518; Y10T 428/31504; Y10T 428/31855; Y10T 428/31533; Y10T 428/31786; Y10T 428/31895; Y10T 428/31971; Y10T 428/31982; A61K 41/0028; A61K 47/6925; A61K 9/0009; A61K 9/1075; A61K 9/5146; B01J 31/00; C07C 303/22; C07C 303/40; C07C 309/24; C07C 311/09; C07C 315/02; C07C 317/22; C07C 319/14; C07C 323/66; C08J 5/2218; C08J 2205/10; C25B 13/08; C25B 1/06; C25B 1/10; C25B 9/10; G01N 21/03; G01N 33/5302; G01N 33/6872; G11C 13/0014; G11C 13/0016; G11C 17/16; G11C 17/165; G11C 2213/51; H05B 33/22

See application file for complete search history.

(56) References Cited

OTHER PUBLICATIONS

Jiang Ruichun et al: "Perfluorocyclobutane and poly(vinylidene fluoride) blend membranes for fuel cells", Electrochimica Acta, vol. 110, Aug. 2, 2013.

Andrew E Feiring et al: "Novel Aromatic Polymers with Pendant Lithium Perfluoroalkylsulfonate or Sulfonimide Groups" Macromolecules, American Chemical Society, vol. 33, No. 25; Jan. 1, 2000.

McLoughlin V C R et al: "A Route to Fluoroalkyl-Substituted Aromatic Compounds Involving Fluoroalkylcopper Intermediates" Tetrahedron, Elsevier Science Publishers, Amsterdam, NL, vol. 25, No. 24, Jan. 1, 1969.

International Search Report dated May 13, 2016.

PROCESS FOR PREPARING UNIPOLAR CATION-CONDUCTING IONOMERS FROM DIFLUORO IONIC MONOMERS

RELATED APPLICATION

This application is a National Phase of PCT/FR2016/051905, filed on Jul. 21, 2016, which in turn claims the benefit of priority from French Patent application No. 15 56967, filed on Jul. 22, 2015 the entirety of which are incorporated by reference.

FIELD OF THE INVENTION

The invention relates to a process for preparing unipolar cation-conducting ionomers from fluoro ionic monomers, to said unipolar cation-conducting ionomers, to the uses thereof, to an electrolytic composition comprising at least one of said unipolar cation-conducting ionomers and to an electrochemical device comprising at least one of said unipolar cation-conducting ionomers, especially as electrolyte.

DESCRIPTION OF THE RELATED ART

Electrochemical energy-storage devices such as lithium batteries have become essential constituents in portable devices such as cell phones, computers and light power tools, or heavier devices such as two-wheel transportation means (bicycles, mopeds) or four-wheel transportation means (electrical or hybrid motor vehicles). They are also widely studied for use in the field of stationary energy storage.

The various constituents of an electrochemical device (e.g. electrode and/or electrolyte materials) are chosen so as to produce, at the lowest possible cost, devices that have high energy density, good cycling stability and which operate with safety.

In terms of rechargeable batteries, lithium batteries are the ones which have the highest theoretical energy densities. In addition, in the field of portable electronics, batteries that are capable of functioning at temperatures as low as −20° C. (253 K) are required. To do this, batteries operating with liquid electrolytes consisting of mixtures of cyclic carbonates, such as ethylene carbonate (EC), and acyclic carbonates such as dimethyl carbonate (DMC), diethyl carbonate (DEC) or ethyl methyl carbonate (EMC), have been developed. The salt predominantly used is lithium hexafluorophosphate ($LiPF_6$) and is generally used at a molar concentration of about 1 mol/l. Several liquid electrolytes are commercial such as LP30® which is a 1M solution of $LiPF_6$ in a 1/1 mixture of EC/DMC. The reactions of the liquid electrolytes with lithium metal, $Li^0$, do not make it possible to obtain a sufficient number of charging/discharging cycles in lithium batteries using $Li^0$ negative electrodes. Replacing $Li^0$ with lithiated graphite, $LiC_6$, at the start of the 1990s allowed the development of lithium-ion batteries. EC and $LiPF_6$ allow the formation of an SEI (Solid Electrolyte Interface) which has the effect of efficiently cycling the graphite electrode. The liquid electrolytes previously mentioned are then used with macroporous polyolefin separators such as those sold under the reference Solupor®, based on polyethylene, or Celgard® (e.g. Celgard 2400), based on polypropylene. The porous phase filled with liquid electrolyte then ensures the ion conductivity, whereas the polymeric phase ensures the mechanical strength by preventing short circuits via contact between the electrodes. The introduction of a separator induces a drop in ion conductivity by a factor ranging from 5 to 20 relative to that obtained in the presence of a liquid electrolyte alone (i.e. without separator). Moreover, the low affinity of the liquid electrolyte, of hydrophilic nature, with the separator, of hydrophobic nature, does not allow very good retention of the liquid electrolyte in the separator, not favouring the formation of thin-film batteries. In addition, although liquid electrolytes are suitable for use at low temperatures, their stability at high temperature is more problematic. Thus, the heat instability of $LiPF_6$ at and above 50-55° C. is well known. It is possible to use lithium salts that are much more heat-stable than $LiPF_6$, such as LiTFSI or lithium triflate, but they induce corrosion of the aluminium current collector of the positive electrode at a potential of greater than or equal to 3.6 V vs $Li/Li^+$. It is possible to overcome this drawback by making use of partially fluorinated solvents, which increase the price of the battery. Ionic liquids with very high heat stability on the one hand give battery performance qualities that are inferior to those of the liquid electrolytes of the prior art and, on the other hand, are very expensive. Consequently, the cost of lithium-ion batteries and the safety problems currently compromise the development of electrical vehicles powered by such lithium-ion batteries.

A second category of electrolytes makes it possible to use negative electrodes of lithium metal $Li^0$, these being polymeric electrolytes which are solutions of salts in macromolecular solvating solvents such as poly(oxyethylene) or a polyether polymer matrix. These polymeric electrolytes, which do not require the use of a separator, largely meet the specifications for electrical traction and stationary applications. Moreover, they may be used with lithium metal $Li^0$ electrodes while at the same time preventing or decreasing the dendritic growth generally observed in the presence of a liquid electrolyte. However, lithium batteries using polymeric electrolytes without incorporation of liquid solvents are unsuitable for the needs of portable electronics.

The cation transport number (e.g. for the $Li^+$ ion in a lithium accumulator) determines the portion of current transported by the cation. In the electrolyte, the lithium salt which is partially dissociated therein ensures the ion conductivity. This partial dissociation induces equilibria between, on the one hand, the associated species (i.e. pairs of ions in contact), which are electrically neutral and do not contribute towards the conductivity of the electrolyte, and, on the other hand, the pairs of ions separated by the solvent and the free ions which determine the conductivity of the electrolytes. When a DC current is applied through the electrolyte, the current is initially transported by the anions and the cations of the dissociated salt. Since the electrodes block the anions, in the stationary state, the movement of the anions by diffusion counterbalances their movement by migration. Only the $Li^+$ cation then becomes responsible for transporting the current. A cation transport number close to unity makes it possible to reduce the polarization at the electrodes during the steps of rapid charging and discharging and thus to obtain a greater energy and power density.

However, in polymer electrolytes constituted of a lithium salt dissolved in a polyether polymer matrix, the fraction of the charge borne by the lithium ions is low (<20% and about 10% for the most conductive polymeric electrolytes).

Doyle et al. [*Electrochimica Acta*, 1994, 39] calculated that an electrolyte having a transport number equal to 1 made it possible to obtain better performance in a battery than an electrolyte with a transport number of 0.2; even if its total conductivity fell by a factor of 10. In the case of high current densities, the dendritic growth starts at the moment when the lithium concentration falls to zero at the surface of the electrode. Next, the dendrites grow at a rate proportional to the anionic mobility [Brissot et al., *J. Power Sources*, 1999, 81-82, 925-929 and Rosso et al., *J. Power Sources*, 2001, 97-98, 804-806].

In liquid electrolytes, the cation transport number is higher than in polymeric electrolytes and ionic liquids (it is predominantly between 0.3 and 0.4). However, it remains below 1 and is a handicap at a high charging/discharging regime.

It is thus essential to be able to significantly increase the cation transport number and to tend towards a value of 1.

Thus, Benrabah et al. [*Electrochim. Acta*, 1995, 40, 2259-2264] described the grafting of a perfluoro sulfonate anion DaaR$_F$SO$_3$Li (i.e. lithium N,N-diallyl-1-amidotetrafluoroethanesulfonate) corresponding to the following formula:

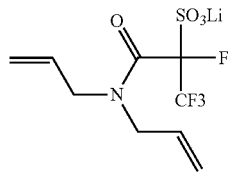

onto polymers of crosslinked polyether type to form a cation-conducting ionomer (i.e. the current is predominantly transported by the Li$^+$ cations) thus having a cation transport number close to 1. However, the polymeric electrolyte obtained has a low ion conductivity of about 4×10$^{-5}$ S·cm$^{-1}$ at 60° C. Moreover, the method for introducing the salt during the crosslinking phase is reflected by grafting yields of about 50%, which, taking into account the cost of the salt, significantly increases the production cost for the ionomer obtained. Finally, the salt that has not been grafted must be extracted and removed (e.g. with solvents) since its allylic double bonds and its amide function reduce its window of electrochemical stability, in oxidation and in reduction, respectively, here also giving rise to an extra production cost and making industrial application problematic.

More recently, Xu et al. [*Chem. Mater.*, 2002, 14, 401-409] described a polymeric electrolyte P(LiOEG$_{q_1}$B) of the oxalato-orthoborate family corresponding to the following formula:

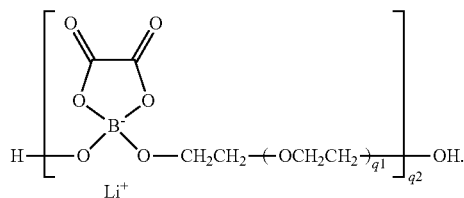

However, LiBOB is sparingly soluble in the standard solvents (0.5 mol/l whereas the standard electrolytes generally use the salt at a concentration close to 1 mol/l). In addition, this salt is water-sensitive. Once incorporated into the polyether backbone by polycondensation, the ionomer obtained retains high sensitivity to hydrolysis. Moreover, the families of polymeric electrolytes based on oxalato- or malonato-orthoborates are generally difficult to purify, the electrolytes prepared always containing lithium bis(oxalato) borate (LiBOB) even after washing several times. The ion conductivity of P(LiOEG$_n$B) is about 1×10$^{-5}$ S·cm$^{-1}$ at room temperature. However, the calculation of this ion conductivity does not take into account the residual content of lithium bis(oxalato)borate, and the conductivity results obtained are thus very probably overestimated and the ion conductivity decreases markedly when the value of n is high (e.g. n≤16). Finally, the ionomers obtained have no mechanical strength.

Objects and Summary

The aim of the present invention is to overcome all or some of the drawbacks of the mentioned prior art and to provide unipolar cation-conducting ionomers which have good properties in terms of ion conduction, cation transport number and mechanical strength, in particular having a cation transport number close to 1, said ionomers being able to be used in total safety in an electrochemical device.

This aim is achieved by the invention that will be described below.

The first subject of the invention is a process for preparing an ionomer comprising at least repeating units UP corresponding to formula (II) below:

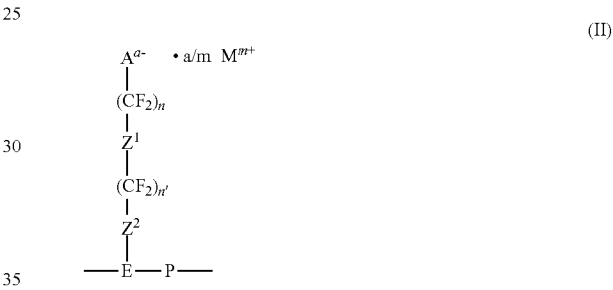

in which:

M is an alkali metal cation, an alkaline-earth metal cation, a transition metal cation, a poor metal cation, an ammonium, a sulfonium or a phosphonium of valency m, with 1≤m≤3, m being an integer, A$^{a-}$ is an anion chosen from a sulfonate anion, a sulfonimide anion of formula —SO$_2$—N$^-$—SO$_2$R, an anion derived from a sulfonimide anion bearing at least two negative charges, and a carbanion of formula —SO$_2$—C$^-$R'R", with 1≤a≤3, a being an integer, with R representing a fluorine atom; an optionally fluoro or perfluoro alkyl group, containing from 1 to 10 carbon atoms, said alkyl group possibly bearing at least one electron-withdrawing group X$^1$; an optionally fluoro or perfluoro alkoxy group, containing from 1 to 10 carbon atoms, said alkoxy group possibly bearing at least one electron-withdrawing group X$^2$; a phenoxy group optionally substituted with an electron-withdrawing group X$^2$; an optionally fluoro or perfluoro dialkyl ether group, containing from 1 to 10 carbon atoms; a thiocyanate group (—SCN); an optionally substituted phenyl group; a nitrile group (—CN); an amino group of formula —NR$^1$R$^2$, in which R$^1$ and R$^2$ are chosen, independently of each other, from the following groups: an optionally fluoro or perfluoro alkyl group, containing from 1 to 5 carbon atoms, an alkyl group containing from 1 to 5 carbon atoms and bearing an electron-withdrawing group X$^3$, an optionally fluoro or perfluoro dialkyl ether group, containing from 1 to 5 carbon atoms, and an electron-withdrawing group X$^4$; a group —NR$^3$ being chosen from a saturated heterocycle containing from 3 to 6 carbon atoms and an unsaturated heterocycle containing from 4 to 6 carbon atoms; an amide group of formula —NH—CO—R$^4$ or —N(CH$_3$)—CO—R$^4$, in which R$^4$ is an alkyl group containing from 1 to 3 carbon atoms; a sulfonamide group of formula —NH—SO$_2$—R$^5$ or —N(CH$_3$)—SO$_2$—R$^5$, in which R$^5$ is an alkyl group containing from 1 to 3 carbon atoms; a urethane group of formula —NH—CO$_2$—R$^6$ or —N(CH$_3$)—CO$_2$—R$^6$, in which R$^6$ is an alkyl group containing from 1 to 3 carbon atoms; a cyanamide group of formula —NH—CN or —N(R$^7$)—CN, in which R$^7$ is an alkyl group containing 1 to 3 carbon atoms; a dicyanamide group —N(CN)$_2$; a tricyanomethyl group —C(CN)$_3$; or a dicyanomethylene group of formula —CH(CN)$_2$ or —CR$^8$(CN)$_2$, in which R$^8$ is an alkyl group containing 1 to 3 carbon atoms, with R' and R" being chosen, independently of each other, from the following monovalent groups: a fluorine atom; a thiocyanate group; a nitrile group; a nitro group; a nitroso group of formula R$^9$NO—, in which R$^9$ is an alkyl group containing from 1 to 3 carbon atoms; a carbonyl group of formula —COR$^{10}$ in which R$^{10}$ is a perfluoro alkyl group containing from 1 to 5 carbon atoms; a sulfoxide group of formula —SOR$^{11}$ in which R$^{11}$ is an optionally fluoro or perfluoro alkyl group, containing from 1 to 5 carbon atoms or an optionally fluoro or perfluoro dialkyl ether group, containing from 1 to 5 carbon atoms; a sulfonyl group of formula —SO$_2$R$^{12}$ in which R$^{12}$ is a fluorine atom, a thiocyanate group, a nitrile group, an optionally fluoro or perfluoro alkoxy group, containing from 1 to 5 carbon atoms, an optionally fluoro or perfluoro alkyl group, containing from 1 to 5 carbon atoms or an optionally fluoro or perfluoro dialkyl ether group, containing from 1 to 5 carbon atoms; a carboxylic ester group of formula —COOR$^{13}$, in which R$^{13}$ is an alkyl group containing from 1 to 5 carbon atoms; an amide group of formula —CONHR$^{14}$ in which R$^{14}$ is an alkyl group containing from 1 to 5 carbon atoms; an amide group of formula —CONR$^{14}$R$^{15}$ in which R$^{14}$ and R$^{15}$ are chosen, independently of each other, and R$^{15}$ is an alkyl group containing from 1 to 5 carbon atoms; an optionally substituted phenyl group; or an optionally substituted phenoxy group, or with R' and R" being divalent groups such that the resulting carbanion radical —C$^-$R'R" forms an aromatic ring comprising from 5 to 6 carbon atoms and optionally one or more heteroatoms O or N, said aromatic ring being optionally substituted with one or more nitrile groups, 1≤n≤4, and preferably 1≤n≤2, and more preferably n=2, n being an integer, 0≤n'≤2, n' being an integer, Z$^1$ is chosen from a single bond, an oxygen atom, a sulfur atom, a group S=O, a group S(=O)$_2$ and a phenyl group optionally substituted in the ortho position relative to one of the functions (CF$_2$)$_n$ or (CF$_2$)$_{n'}$, Z$^2$ is chosen from a single bond, an oxygen atom, a sulfur atom, a group S=O, a group S(=O)$_2$ and a group C=O, it being understood that when n'=0, Z$^2$ is a single bond, E is an aromatic group comprising from 5 to 20 carbon atoms, and preferably from 5 to 15 carbon atoms, it being understood that E comprises from 1 to 3 aromatic rings, and P is an alkylene oxide polymer chain, said process being characterized in that it comprises at least one step a$_1$) of polycondensation of at least one difluoro ionic monomer (I) with at least one alkylene oxide polymer P$^1$ in basic medium, said difluoro ionic monomer corresponding to formula (I) below:

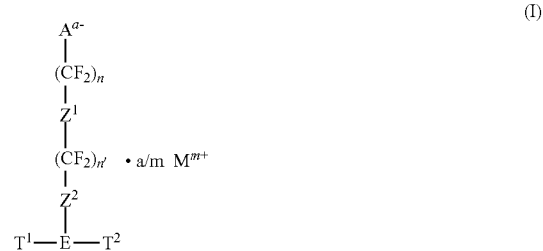

in which A, n, n', Z$^1$, Z$^2$, E, m, a and M are as defined above and T$^1$ and T$^2$ are fluorine atoms.

The ionomer of the invention may comprise p units UP, preferably at least 2 units UP, especially with 2≤p≤100, and more preferably 2≤p≤50.

The difluoro ionic monomers (I) used in the process of the invention have a high capacity for dissociation and have the advantage of being able to lead simply and economically to unipolar cation-conducting ionomers, especially having good electrochemical and mechanical performance, particularly in terms of ion conduction, cation transport number and mechanical strength.

It should be noted that the polycondensation, by comparison with other types of polymerization (e.g. radical polymerization), generally requires starting monomers of very high purity and that are sufficiently reactive so as to lead quantitatively to the desired polymer. Moreover, polycondensation, by comparison with radical polymerization, makes it possible to form repeating units UP as defined above or, in other words, an ionomer which contains an alternation of: ionic group E-Z$^2$—(CF$_2$)$_n$—Z$^1$—(CF$_2$)$_{n'}$-A$^{a+}$.(a/m) M$^{m+}$/alkylene oxide polymer chain/ionic group E-Z$^2$—(CF$_2$)$_n$—Z$^1$—(CF$_2$)$_{n'}$-A$^{a+}$.(a/m) M$^{m+}$/alkylene oxide polymer chain, etc. Specifically, with radical polymerization, the difference in reactivity between the starting monomers does not make it possible to obtain such an alternation and leads to homopolymerization or to the production of comb polymers, inducing the presence of adjacent ionic groups. However, the presence of adjacent ionic groups reduces the dissociation and, consequently, the ion conductivity of the polymer obtained. Polycondensation also makes it possible to know with precision the position of the ionic groups.

In the present case, the polycondensation of a difluoro ionic monomer (I) with an alkylene oxide polymer P$^1$ is simple, readily industrializable and can give quantitatively cation-conducting ionomers, especially by virtue of the presence of the highly reactive fluorine atoms (i.e. T$_1$=T$_2$=F) on the starting ionic monomer.

Specifically, the use of dihydroxy ionic monomers (replacement of the fluorine atoms with hydroxyl groups) as precursors in the polycondensation does not lead to the ionomers of the invention in good yields. Specifically, the difluoro ionic monomers may be directly polymerized with commercial alkylene oxide polymers P$^1$, whereas the corresponding dihydroxy ionic monomers require additional steps, especially for conversion of said P$^1$ (generally ending in —OH) so as to functionalize it with halogen atoms or other functions that are capable of reacting with the two hydroxyl functions of said dihydroxy ionic monomers. It is therefore not envisageable at the present time on an industrial scale.

In particular, the ionic monomers (I) used in the process of the present invention have the advantage of having three key functions on the aromatic group E: an ionic function —$Z^2$—$(CF_2)_n$—$Z^1$—$(CF_2)_n$-$A^{a-}$.(a/m) $M^{m+}$ and two fluorine atoms (functions $T^1$ and $T^2$). The ionic function makes it possible to improve their dissociation in aprotic medium by virtue of their very sparingly basic nature; and the fluorine atoms allow their polymerization or copolymerization with monomers or oligomers, especially based on alkylene oxide chains, and thus enable them to be excellent unipolar cation-conducting ionomer precursors bearing a solvating polyether backbone especially having a low glass transition temperature $T_g$.

In the present invention, the expression "alkyl group" means a linear, branched or cyclic alkyl group (i.e. constituted of carbon and hydrogen atoms), and preferably a linear alkyl group.

In the present invention, the expression "alkoxy group" means a linear, branched or cyclic alkoxy group, and preferably a linear alkoxy group.

In the present invention, the expression "dialkyl ether group" means a dialkyl ether group in which the two alkyl groups are chosen, independently of each other, from linear, branched and cyclic alkyl groups, and are preferably two linear alkyl groups.

The optionally fluoro or perfluoro alkyl group R preferably contains 1 to 5 carbon atoms.

According to one embodiment of the invention, the optionally fluoro or perfluoro alkyl group R is a linear alkyl group, chosen especially from:

a linear alkyl group containing from 1 to 5 carbon atoms, and preferably containing from 1 to 3 carbon atoms, such as —$CH_3$ or —$C_2H_5$, a perfluoro linear alkyl group containing from 1 to 8 carbon atoms, and preferably containing from 1 to 4 carbon atoms, such as —$CF_3$, —$C_2F_5$ or —$C_4F_9$, and a fluoro linear alkyl group of formula —$CH_2$—$C_uF_{2u+1}$, in which $1 \leq u \leq 5$, and preferably u=1 or 2, such as —$CH_2CF_3$.

The electron-withdrawing group $X^1$ may be a nitrile group (—CN), a —$CF_3$ group or a nitro group (—$NO_2$).

By way of example of optionally fluoro or perfluoro alkyl group R, containing from 1 to 10 carbon atoms and bearing at least one electron-withdrawing group $X^1$, mention may be made of a linear alkyl group containing 1 or 2 carbon atoms and bearing at least one nitrile or nitro group, such as —$CH_2CN$, —$CH_2NO_2$, —$CH(CN)_2$ or —$C(CN)_3$.

The optionally fluoro or perfluoro alkoxy group R preferably contains 1 to 6 carbon atoms.

The electron-withdrawing group $X^2$ may be a nitrile group, a —$CF_3$ group or a nitro group.

By way of example of optionally fluoro or perfluoro alkoxy group R containing from 1 to 10 carbon atoms and bearing at least one electron-withdrawing group $X^2$, mention may be made of a linear alkoxy group containing from 2 to 4 carbon atoms, and preferably containing 2 carbon atoms, and bearing at least one electron-withdrawing group $X^2$, such as —$OC_2H_4CN$ or —$OC_2H_4NO_2$.

According to one embodiment of the invention, the optionally fluoro or perfluoro alkoxy group R containing from 1 to 10 carbon atoms is a group chosen from:

a linear alkoxy group containing from 1 to 5 carbon atoms, and preferably containing from 1 to 3 carbon atoms, such as —$OCH_3$ or —$OC_2H_5$, a perfluoro linear alkoxy group containing from 1 to 8 carbon atoms, and preferably containing from 1 to 4 carbon atoms, a fluoro linear alkoxy group of formula —O—$CH_2$—$C_{w'}F_{2w'+1}$, in which $1 \leq w' \leq 5$, and preferably w'=1 or 2, such as —$OCH_2CF_3$, and a fluoro branched alkoxy group of formula —O—CH($C_tF_{2t+1}$)($C_{t'}F_{2t'+1}$), in which $1 \leq t \leq 3$, and preferably t=1 or 2, $1 \leq t' \leq 3$, and preferably t'=1 or 2, such as —$OCH(CF_3)_2$.

The phenoxy group R optionally substituted with an electron-withdrawing group $X^2$ may correspond to the formula —$OC_6H_5$ or to the formula —$OC_6H_4X^2$ in which $X^2$ is as defined in the present invention, said phenyl group being substituted with the group $X^2$ in the para, ortho or meta position, and preferably in the para or ortho position.

The optionally fluoro or perfluoro dialkyl ether group R preferably contains 1 to 5 carbon atoms, especially when the alkyl groups are linear or branched.

According to one embodiment of the invention, the optionally fluoro or perfluoro dialkyl ether group R, containing from 1 to 10 carbon atoms, is a linear dialkyl ether group, chosen especially from:

a linear dialkyl ether group of formula —$C_vH_{2v}OC_wH_{2w+1}$ in which $1 \leq v \leq 5$, and preferably $2 \leq v \leq 4$, and $1 \leq w \leq 4$, and preferably w=1 or 2, and a perfluoro linear dialkyl ether group of formula —$C_uF_{2u}OC_{v'}F_{2v'+1}$, in which $1 \leq u' \leq 5$, and preferably $2 \leq u' \leq 4$, and $1 \leq v' \leq 4$, and preferably v'=1 or 2, such as —$CF_2CF_2OCF_2CF_3$.

By way of example of substituted phenyl group R, mention may be made of a phenyl group substituted with a nitro group, a nitrile group, a fluorine atom or a methanesulfonyl group (—$SO_2CH_3$), said phenyl group being substituted in the para and/or ortho and/or meta position.

According to a preferred embodiment of the invention, the optionally fluoro or perfluoro group $R^1$ (or, respectively, group $R^2$), containing from 1 to 5 carbon atoms, is a linear alkyl group, especially a methyl group or an ethyl group.

The electron-withdrawing group $X^3$ may be a nitrile group, a nitro group or a thiocyanate group, and more generally a substituent having positive para or meta Hammett sigma values and preferably greater than 0.3.

The alkyl group $R^1$ (or, respectively, group $R^2$) containing from 1 to 5 carbon atoms and bearing an electron-withdrawing group $X^3$ is preferably a group of formula —$(CH_2)_rCN$ or —$(CH_2)_rNO_2$, in which r=1 or 2.

The optionally fluoro or perfluoro dialkyl ether group $R^1$ (or, respectively, group $R^2$) containing from 1 to 5 carbon atoms, is preferably a —$(CH_2)_2OCH_3$ group.

The electron-withdrawing group $X^4$ may be a nitrile group or a nitro group.

In one advantageous embodiment of the invention, the amino group —$NR^1R^2$ is preferably chosen from the following groups: —$N(CH_3)C_2H_5$, —$N(CH_3)_2$, —$N(C_2H_5)_2$, —$N[(CH_2)_2CN]_2$, —$N(CH_2CN)_2$, —$N[(CH_2)_2CN]$ [$CH_2CN$], —$N[(CH_2)_2OCH_3]_2$, —$N[(CH_2)_2OCH_3]$ [$CH_2CN$], —$N[(CH_2)_2OCH_3][(CH_2)_2CN]$, —$N(CH_3)CN$, —$N(C_2H_5)CN$, —$N(CN)_2$, —$N[(CH_2)_2NO_2]_2$, —$N(CH_2NO_2)_2$, —$N[(CH_2)_2NO_2][CH_2NO_2]$, —$N[(CH_2)_2OCH_3][CH_2NO_2]$, —$N[(CH_2)_2OCH_3][(CH_2)_2NO_2]$, —$N(CH_3)NO_2$, —$N(C_2H_5)NO_2$ and —$N(NO_2)_2$.

As saturated heterocycle —$NR^3$ containing from 3 to 6 atoms, mention may be made of aziridine, azetidine, pyrrolidine or piperidine.

As unsaturated heterocycle —$NR^3$ containing from 4 to 6 atoms, mention may be made of pyrrolidone, pyrrole, imidazole, pyrazole, triazole, tetrazole, succinimide or maleimide.

The amide group of formula NH—CO—$R^4$ or —N($CH_3$)—CO—$R^4$ may be cyclic or linear.

According to a preferred embodiment of the invention, the group R is a perfluoro alkyl group, such as —$CF_3$.

The group $R^{10}$ is preferably a perfluoro linear alkyl group, such as —$CF_3$ or —$C_2F_5$.

The group $R^1$ is preferably an optionally perfluoro linear alkyl group, such as —$CH_3$, —$C_2H_5$, —$CF_3$ or —$C_2F_5$.

The group $R^{12}$ is preferably an optionally perfluoro linear alkyl group, such as —$CH_3$, —$C_2H_5$, —$CF_3$ or —$C_2F_5$; or a perfluoro linear dialkyl ether group such as —$CF_2OCF_3$, —$CF_2OC_2F_5$, —$C_2F_4OC_2F_5$ or —$C_2F_4OCF_3$; or a linear alkoxy group such as —$OCH_3$ or —$OC_2H_5$.

By way of example of substituted phenyl group R' or R", mention may be made of a phenyl group mono-, di- or tri-substituted with one or more of the following groups: a fluorine atom, a nitrile group, a nitro group, a nitroso group or a carbonyl group of formula —C(=O)$R^{10}$ as defined previously, a carboxylic ester group of formula —$COOR^{13}$ as defined previously, an amide group of formula —$CONHR^{14}$ as defined previously, an amide group of formula —$CONR^{14}R^{15}$ as defined previously, or a group of formula —$SO_2X^5$ in which $X^5$ is a fluorine atom, —$CF_3$, —SCN or —$CH_3$. The phenyl group R' or R" may be substituted in the ortho and/or meta and/or para position, and preferably in the para position.

By way of example of substituted phenoxy group R' or R", mention may be made of a phenoxy group mono-, di- or tri-substituted with one or more of the following groups: a fluorine atom, a nitrile group, a nitro group, a nitroso group, a group of formula —$SO_2X^5$ as defined previously, or a carbonyl group of formula —C(=O)$R^{10}$ as defined previously. The phenoxy group R' or R" may be substituted in the ortho and/or meta and/or para position, and preferably in the para position.

The group —$C^-R'R''$ forming an aromatic ring comprising from 5 to 6 carbon atoms and optionally one or more of the heteroatoms O or N, said aromatic ring being optionally substituted with one or more nitrile groups, may be one of the following groups:

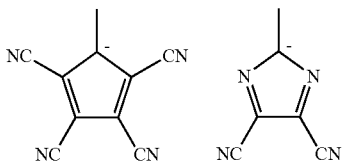

When these carbanions are attached to the $SO_2$ group, a very acidic compound is obtained, the conjugate base of which is doubly stabilized: 1) by the aromaticity of the anion, and 2) by the extension of the conjugation to the nitrile groups. The acid formed is thus very acidic and readily transformable into a salt.

An anion derived from a sulfonimide anion bearing at least two negative charges (i.e. a=2 or 3) is a sulfonimide anion —$SO_2$—$N^-$—$SO_2$—Y in which Y is a chemical group bearing one or two negative charges.

The anion derived from a sulfonimide anion bearing at least two negative charges (i.e. a=2 or 3) may be chosen from the anions having the following formulae: —$SO_2$—$N^-$—$SO_2$—$N^-$—$SO_2CF_3$, —$SO_2$—$N^-$—$SO_2$—$N^-$—$(CF_2)_{n''}$—$SO_3^-$ with 2≤n"≤4, —$SO_2$—$N^-$—$SO_2$—Ar—$SO_3^-$ with Ar being a phenyl group optionally substituted with 2, 3 or 4 fluorine atoms and preferably 4 fluorine atoms, —$SO_2$—$N^-$—$SO_2$—Ar—$SO_2$—$N^-$—$SO_2CF_3$, —$SO_2$—$N^-$—$SO_2$—$N^-$—$SO_2$—$C^-R'R''$, with R' and R" being as defined in the invention.

With such an anion bearing at least two negative charges, the CEI may be multiplied by a factor of 2 or 3 without increasing the concentration of ionic monomer, while at the same time moderately increasing its molar mass.

According to a particularly preferred embodiment of the invention, the anion $A^{a-}$ is a sulfonate or a sulfonimide (i.e. with a=1), and more preferably a sulfonimide.

Specifically, the monomers in which $A^{a-}$ is a sulfonimide lead to ionomers whose stability to oxidation and whose ion conductivity are improved.

The aromatic group E may comprise non-aromatic components (known as "functional" components) present on one or more of the aromatic rings or making it possible to attach several aromatic rings together. These non-aromatic components may be alkyl, alkenyl, alkynyl, haloalkyl, conjugated dienyl, alcohol, ether, carboxylic acid, ketone, ester, amide, amine, nitro, etc. groups.

For example, the benzophenone group is a $C_{13}$ aromatic group E (i.e. comprising 13 carbon atoms) comprising two aromatic rings (i.e. two phenyl groups) and one non-aromatic component (i.e. ketone group); the benzyl group is a $C_7$ aromatic group E (i.e. comprising 7 carbon atoms) comprising one aromatic ring (i.e. a phenyl group) and one non-aromatic component (i.e. a methylene group).

In the present invention, the aromatic group E may comprise heteroatoms such as one or more nitrogen, sulfur or oxygen atoms, or may be constituted solely of carbon and hydrogen atoms.

In the present invention, the term "aromatic ring" means a cyclic structure containing [4r'+2] delocalized electrons, with r'=1.

Preferably, the aromatic group E comprises at least one aromatic ring which is a phenyl group, a thienyl group, a pyridyl group, a furyl group, or a pyrazolyl group, and preferably a phenyl group.

The aromatic rings of the aromatic group E may be chosen, independently of each other, from a phenyl group, a thienyl group, a pyridyl group, a furyl group and a pyrazolyl group.

E preferably comprises one or two aromatic rings.

The aromatic ring(s) of the aromatic group E are preferably phenyl groups.

When E comprises two aromatic rings, it may be an azulenyl group, a benzophenone group, a diphenyl group, a diphenyl sulfide group, a diphenyl sulfone group or a naphthyl group, and preferably a benzophenone group, a diphenyl sulfide group or a diphenyl sulfone group.

When E comprises three aromatic rings, it may be an anthracenyl or a phenanthrenyl group.

Preferably, E is an aromatic group which generates little steric hindrance, i.e. it does not comprise any carbon tri-substituted with aromatic rings such as a triphenylmethyl group (trityl group).

The fluorine atoms $T^1$ and $T^2$ are preferably on at least one aromatic ring of the aromatic group E, and more preferably on only one aromatic ring or two different aromatic rings.

In other words, the fluorine atoms $T^1$ and $T^2$ are substituents on at least one aromatic ring of the aromatic group E, and more preferably on only one aromatic ring or two different aromatic rings.

In particular, when E comprises several aromatic rings, the groups $T^1$ and $T^2$ may be (i.e. as substituents) either on the same aromatic ring, or on different aromatic rings of the group E.

Thus, when the fluorine atoms $T^1$ and $T^2$ are substituents of aromatic ring(s) of the aromatic group E, the process of the invention leads to an ionomer in which the alkylene oxide polymer chain is directly attached to the aromatic ring(s) of the group E (via end groups of the alkylene oxide polymer $P^1$ or terminal heteroatoms of the alkylene oxide polymer chain).

This direct bonding makes it possible to improve the conductivity of the ionomer obtained and to obtain very good yields.

In a preferred embodiment of the invention, the function $-Z^2-(CF_2)_{n'}-Z^1-(CF_2)_n-A^{a-}.(a/m)\ M^{m+}$ is a substituent of an aromatic ring of the group E.

In a particularly preferred embodiment of the invention, at least two of the three functions $-Z^2-(CF_2)_{n'}-Z^1-(CF_2)_n-A^{a-}.(a/m)\ M^{m+}$, $T^1$ and $T^2$ are on the same aromatic ring of the group E (i.e. as substituents).

In a preferred embodiment of the invention, E is chosen from a phenyl group, a benzophenone group, a diphenyl sulfide group and a diphenyl sulfone group.

In the difluoro ionic monomer of formula (I), the transition metal M may be a transition metal from period 4 or 5 of the Periodic Table of the Elements, in particular a transition metal chosen from iron, copper, zinc, cobalt, nickel and silver.

The iron may be trivalent or divalent (m=3 or 2); the copper, zinc, cobalt and nickel are divalent (m=2) and the silver is monovalent (m=1).

The poor metal may be aluminium. Aluminium is trivalent (m=3).

M is preferably an alkali metal cation, such as $Li^+$, $Na^+$ or $K^+$ (m=1) or an alkaline-earth metal cation, such as $Mg^{2+}$ or $Ca^{2+}$, and more preferably an alkali metal cation, such as $Li^+$ or $Na^+$.

As ammonium cation, M may be a compound of formula $^+NR^{16}R^{16'}R^{16''}R^{16'''}$ or $^+NHR^{16}R^{16'}R^{16''}$ in which $R^{16}$, $R^{16'}$, $R^{16''}$ and $R^{16'''}$ are identical or different alkyl groups, containing from 1 to 4 carbon atoms.

The ionomers bearing ammonium cations $^+NHR^{16}R^{16'}R^{16''}$ may be advantageously impregnated with ionic liquids.

As sulfonium cation, M may be a compound of formula $^+SR^{16}R^{16'}R^{16''}$ or $^+SHR^{16}R^{16'}$ in which $^-R^{16}$, $R^{16'}$ and $R^{16''}$ are as defined previously.

As phosphonium cation, M may be a compound of formula $^+PR^{16}R^{16'}R^{16''}R^{16'''}$ or $^+PHR^{16}R^{16'}R^{16''}$ in which $R^{16}$, $R^{16'}$, $R^{16''}$ and $R^{16'''}$ are as defined previously.

According to one embodiment of the invention, $n'\ne 0$.

The difluoro ionic monomer (I) of the invention may be such that $Z^1$ is an oxygen atom and $Z^2$ is a sulfur atom or a single bond.

According to a particularly preferred embodiment of the invention, one or more of the following conditions apply to the difluoro ionic monomer (I) of the invention:

n=n'=2, $Z^1$ is an oxygen atom, $Z^2$ is a sulfur atom or a single bond.

As examples of such difluoro ionic monomers (I), mention may be made of the monomers corresponding to the following formulae:

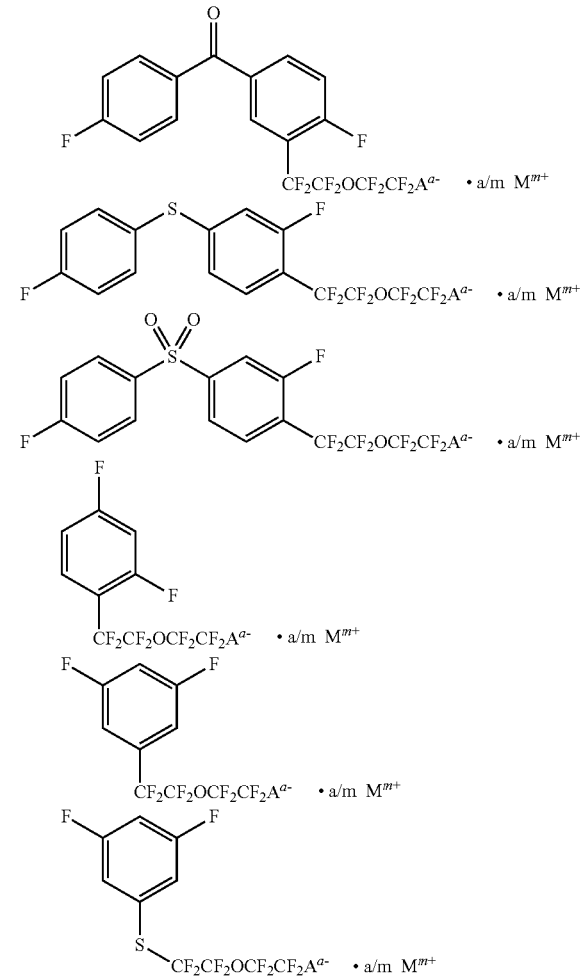

in which M, A, a and m are as defined in the invention.

The polycondensation step $a_1$) makes it possible to modify the distance between the ionic functions and thus to control the viscosity and/or the molar mass of the desired ionomer. For example, increasing the space between the ionic functions makes it possible to improve the ion conductivity of said ionomer. Consequently, a certain solvating chain length (i.e. of alkylene oxide polymer chain P) is preferable so that each ionic function is suitably solvated.

The alkylene oxide polymer chain P of the unit UP may comprise terminal heteroatoms such as an oxygen atom (—O—), sulfur atom (—S—), secondary amine (—NH—) or tertiary amine (—$NR^{17}$—, $R^{17}$=—$CH_3$ or —$C_2H_5$), and preferably such as an oxygen atom or a secondary amine.

As a result, the alkylene oxide polymer $P^1$ may comprise end groups such as hydroxyl (—OH), thiol (—SH), primary amine (—$NH_2$) or secondary amine (—$NHR^{17}$, $R^{17}$=—$CH_3$ or —$C_2H_5$), and preferably such as hydroxyl or primary amine.

The alkylene oxide polymer $P^1$ used in step a) may be chosen from the polymers having the following formulae:

$$H-[O-(CH_2)_x]_y-OH,$$

in which $2 \le x \le 4$, $1 \le y \le 50$, preferably $2 \le y \le 40$, and more preferably $8 \le y \le 34$, $$H-[O-CH_2-CHR^{18}]_y-OH,$$

in which $R^{18}$ is an alkyl group containing from 1 to 8 carbon atoms, and preferably a methyl group, or an alkoxy group containing from 1 to 8 carbon atoms, and preferably a methoxy group, and $1 \leq y \leq 50$, preferably $2 \leq y \leq 40$, and more preferably $8 \leq y \leq 34$,

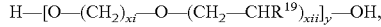
H—[O—(CH$_2$)$_{xi}$—O—(CH$_2$—CHR$^{19}$)$_{xii}$]$_y$—OH, which $1 \leq xi \leq 4$, and preferably xi=1; $1 \leq xii \leq 2$, and preferably xii=1; $R^{19}$ is a hydrogen atom or an alkyl group containing from 1 to 8 carbon atoms, and preferably a hydrogen atom or a methyl group; $1 \leq y \leq 50$, preferably $2 \leq y \leq 40$, and more preferably $8 \leq y \leq 34$,

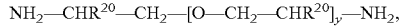
NH$_2$—CHR$^{20}$—CH$_2$—[O—CH$_2$—CHR$^{20}$]$_y$—NH$_2$, in which $R^{20}$ is an alkyl group containing from 1 to 8 carbon atoms, and preferably a methyl group; and $1 \leq y \leq 50$, preferably $2 \leq y \leq 40$, and more preferably $8 \leq y \leq 34$, these oligomers being sold under the name Jeffamines® in a wide range of y when $R^{20}$ is a CH$_3$, and

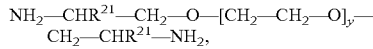
NH$_2$—CHR$^{21}$—CH$_2$—O—[CH$_2$—CH$_2$—O]$_y$—
 CH$_2$—CHR$^{21}$—NH$_2$, in which $R^{21}$ is an alkyl group containing form 1 to 8 carbon atoms, and preferably a methyl group; and $1 \leq y \leq 50$, preferably $2 \leq y \leq 40$, and more preferably $8 \leq y \leq 34$.

Use may also be made, as $P^1$, of a triblock copolymer corresponding to the following formula:

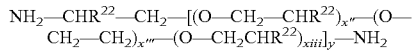
NH$_2$—CHR$^{22}$—CH$_2$—[(O—CH$_2$—CHR$^{22}$)$_{x''}$—(O—
 CH$_2$—CH$_2$)$_{x'''}$—(O—CH$_2$CHR$^{22}$)$_{xiii}$]$_y$—NH$_2$ in which $R^{22}$ is an alkyl group containing from 1 to 8 carbon atoms, and preferably a methyl group; $1 \leq x'' \leq 50$, and preferably $5 \leq x'' \leq 24$; $1 \leq x''' \leq 50$, and preferably $8 \leq x''' \leq 34$; $1 \leq xiii \leq 50$, and preferably $5 \leq xiii \leq 24$; $1 \leq y \leq 50$, preferably $2 \leq y \leq 40$, and more preferably $8 \leq y \leq 34$.

The alkylene oxide polymer $P^1$ used in step $a_1$) is preferably a polymer corresponding to one of the following formulae as defined in the invention: H—[O—(CH$_2$)$_x$]$_y$—OH, H—[O—CH$_2$—CHR$^{18}$]$_y$—OH or H—[O—(CH$_2$)$_{xi}$—O—(CH$_2$—CHR$^{19}$)$_{xii}$]$_y$—OH.

In this particular embodiment, the alkylene oxide polymer chain P of the unit UP corresponding to formula (II) may then correspond to any one of the following formulae:

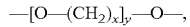
—[O—(CH$_2$)$_x$]$_y$—O—, in which $2 \leq x \leq 4$, $1 \leq y \leq 50$, preferably $2 \leq y \leq 40$, and more preferably $8 \leq y \leq 34$,

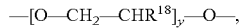
—[O—CH$_2$—CHR$^{18}$]$_y$—O—, in which $R^{18}$ is an alkyl group containing from 1 to 8 carbon atoms, and preferably a methyl group, or an alkoxy group containing from 1 to 8 carbon atoms, and preferably a methoxy group, and $1 \leq y \leq 50$, preferably $2 \leq y \leq 40$, and more preferably $8 \leq y \leq 34$,

—[O—(CH$_2$)$_{xi}$—O—(CH$_2$—CHR$^{19}$)$_{xii}$]$_y$—O—, in which $1 \leq xi \leq 4$, in which $1 \leq xi \leq 4$, and preferably xi=1; $1 \leq xii \leq 2$, and preferably xii=1; $R^{19}$ is a hydrogen atom or an alkyl group containing from 1 to 8 carbon atoms, and preferably a hydrogen atom or a methyl group; $1 \leq y \leq 50$, preferably $2 \leq y \leq 40$, and more preferably $8 \leq y \leq 34$,

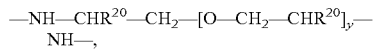
—NH—CHR$^{20}$—CH$_2$—[O—CH$_2$—CHR$^{20}$]$_y$—
 NH—, in which $R^{20}$ is an alkyl group containing from 1 to 8 carbon atoms, and preferably a methyl group; and $1 \leq y \leq 50$, preferably $2 \leq y \leq 40$, and more preferably $8 \leq y \leq 34$, or

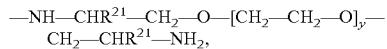
—NH—CHR$^{21}$—CH$_2$—O—[CH$_2$—CH$_2$—O]$_y$—
 CH$_2$—CHR$^{21}$—NH$_2$, in which $R^{21}$ is an alkyl group containing from 1 to 8 carbon atoms, and preferably a methyl group; and $1 \leq y \leq 50$, preferably $2 \leq y \leq 40$, and more preferably $8 \leq y \leq 34$.

Mention may also be made of an alkylene oxide polymer chain P corresponding to the following formula:

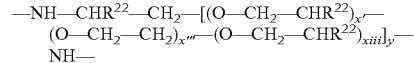
—NH—CHR$^{22}$—CH$_2$—[(O—CH$_2$—CHR$^{22}$)$_{x'}$—
 (O—CH$_2$—CH$_2$)$_{x''}$—(O—CH$_2$—CHR$^{22}$)$_{xiii}$]$_y$—
 NH— in which $R^{22}$ is an alkyl group containing from 1 to 8 carbon atoms, and preferably a methyl group; $1 \leq x'' \leq 50$, and preferably $5 \leq x'' \leq 24$; $1 \leq x''' \leq 50$, and preferably $8 \leq x''' \leq 34$; $1 \leq xiii \leq 50$, and preferably $5 \leq xiii \leq 24$; $1 \leq y \leq 50$, preferably $2 \leq y \leq 40$, and more preferably $8 \leq y \leq 34$.

The alkylene oxide polymer chain P is preferably a chain corresponding to one of the formulae as defined above: —[O—(CH$_2$)$_x$]$_y$—O—, —[O—CH$_2$—CHR$^{18}$]$_y$—O— or —[O—(CH$_2$)$_{xi}$—O—(CH$_2$—CHR$^{19}$)$_{xii}$]$_y$—O—.

In one embodiment of the invention, step $a_1$) involves the polycondensation of a difluoro ionic monomer (I) with an alkylene oxide polymer in basic medium. In this case, an ionomer of formula (III-a) or (III-a') as defined below is obtained.

Step $a_1$) may involve the polycondensation of a difluoro ionic monomer (I) with several (e.g. two or three) different alkylene oxide polymers in basic medium.

For example, the difluoro ionic monomer (I) may react with $P^1$, $P^{1'}$ and optionally $P^{1''}$, with $P^{1'}$ and $P^{1''}$ having the same definition as $P^1$, and $P^1$, $P^{1'}$, $P''$ being different.

In this case, a statistical ionomer is obtained (e.g. ionomer of formula (III-b$_1$) as defined below) comprising repeating units UP, UP', and optionally UP'', with P' and P'' having the same definition as P, and P, P', P'' different. The units UP, UP' and UP'' are distributed statistically in the ionomer formed.

Step $a_1$) may involve the polycondensation of several different difluoro ionic monomers (as defined in the invention) with an alkylene oxide polymer $P^1$ in basic medium.

For example, the polymer $P^1$ may react with a difluoro ionic monomer (I), a difluoro ionic monomer (I') and optionally a difluoro ionic monomer (I''), formulae (I') and (I'') having the same definition as that of formula (I), and the three monomers being different.

In this case, a statistical ionomer is obtained (e.g. ionomer of formula (III-b$_2$) as defined below) comprising repeating units UP$_I$, UP'$_I$, and optionally UP''$_I$, with (I') and (I'') having the same definition as that of (I), and the three monomers being different. The units UP$_I$, UP'$_I$ and UP''$_I$ are distributed statistically in the ionomer formed.

Step $a_1$) may be followed by several other steps involving: either other difluoro ionic monomers different from the difluoro ionic monomer of step $a_1$), or other alkylene oxide polymers different from the alkylene oxide polymer $P^1$ of step $a_1$). These steps are detailed below.

The process may also comprise, after step $a_1$), several other steps $a_i$) different from polycondensation of the difluoro ionic monomer (I) used in step a) with several alkylene oxide polymers different from $P^1$ (e.g. with $P^{1'}$, and optionally $P^{1''}$ as defined previously).

For example, the difluoro ionic monomer (I) may be polycondensed with the alkylene oxide polymer $P^1$ according to step $a_1$), and then with $P^{1'}$ as defined previously according to step $a_2$), and then optionally with $P^{1''}$ as defined previously according to step $a_3$).

In this case, blocks of repeating units (UP)$_p$, (UP')$_{p'}$ and (UP'')$_{p''}$ are formed separately according to the separate steps $a_1$), $a_2$) and $a_3$), and said blocks are then polycondensed in a step a') subsequent to the final step $a_i$) (i.e. $a_3$)

in the present case) to form a block ionomer (e.g. ionomer of formula (III-$c_1$) as defined below).

The process may also involve, after step $a_1$), several other steps $A_i$) different from polycondensation of the alkylene oxide polymer $P^1$ used in step $a_1$) with several difluoro ionic monomers as defined in the invention and different from the one used in step $a_1$) (e.g. with the monomer of formula (I'), and optionally the monomer of formula (I") as defined previously).

For example, the alkylene oxide polymer $P^1$ may be polycondensed with the difluoro ionic monomer (I) in step $a_1$), and then with the difluoro ionic monomer (I') in step $A_2$), and then optionally with the difluoro ionic monomer (I") in step $A_3$).

In this case, blocks of repeating units $(UP_l)_p$, $(UP'_l)_{p'}$ and $(UP''_l)_{p''}$ are formed separately in the separate steps $a_1$), $A_2$) and $A_3$), and said blocks are then polycondensed in a step A') subsequent to the final step $A_i$) (i.e. $A_3$ in the present case) to form a block ionomer (e.g. ionomer of formula (III-$c_2$) as defined below).

The process may also comprise, after step $a_1$), a step a) of polycondensation of the ionomer derived from step $a_1$) with an alkylene oxide polymer $P^{1'}$ as defined previously. An ionomer of formula (III-$d_1$) as defined below is then obtained.

The process may also comprise, after step a), a step α') of polycondensation of the ionomer derived from step $a_1$) with a difluoro ionic monomer (I') as defined previously. An ionomer of formula (III-$d_2$) as defined below is then obtained.

The ionomers of the invention obtained (statistic, alternating or block) may thus comprise two or three different alkylene oxide polymer chains, for example ethylene oxide polymer chains of formula —[O—$CH_2$—$CH_2$]$_y$—O— and/or trimethylene oxide chains —[O—$CH_2$—$CH_2$—$CH_2$]$_y$—O— and/or propylene oxide chains —[O—$CH_2$—$CHCH_3$]$_y$—O—.

According to a first variant of the process of the invention, the process may also comprise after step $a_1$), or optionally after any one of the steps $a_i$), a'), $A_i$), A'), α) or α') if it exists, at least one step b) of placing the ionomer in contact with a compound G comprising at least two functions $F^1$ that are capable of polycondensing with said ionomer and optionally at least one post-polymerizable function $F^2$.

Step b) is consequently a step of polycondensation of the ionomer with compound G. It makes it possible especially to give the ionomer of formula (III-e) or (III-e') as defined below.

The function $F^1$ may be a halogen atom such as a chlorine atom, an isocyanate function or a carboxylate function.

By way of example, compound G comprising at least two functions $F^1$ may be a diisocyanate, a triisocyanate, a di- or trihalo compound, or any other compound comprising two or more functions $F^1$ that are capable of reacting with the alkylene oxide polymer chain P of the ionomer of step $a_1$) or optionally of any one of the steps $a_i$), a'), $A_i$), A'), α) or α') if it exists, and especially with the end groups of said chain, according to a polycondensation.

The diisocyanate may be an alkylene diisocyanate such as hexamethylene diisocyanate (HMDI), a toluene diisocyanate (TDI) (e.g. 2,4-diisocyanate, toluene 2,6-diisocyanate), an oligo(oxy-alkylene) α,ω-diisocyanate (for example a PEG α,ω-diisocyanate or a PTHF α,ω-diisocyanate).

In particular, the compounds G of diisocyanate or triisocyanate type may be polycondensed with the alkylene oxide polymer chain P to give polyurethanes (when the end groups are alcohols) or polyureas (when the end groups are primary amines).

In the present invention, the term "post-polymerizable function $F^{2'''}$" means a function which does not react with the alkylene oxide polymer chain P of the ionomer of step $a_1$) or optionally of any one of the steps $a_i$), a'), $A_i$), A'), α) or α') if it exists, and especially with the end groups of said chain, but which may allow a subsequent polymerization to be performed (e.g. ionic polymerization, radical polymerization or polycondensation).

By way of example of compound G comprising at least two functions $F^1$ and one post-polymerizable function $F^2$, mention may be made of 3-chloro-2-chloroprop-1-ene or the Z and E isomers (i.e. cis and trans) of 1,4-dibromobut-2-ene.

3-Chloro-2-chloroprop-1-ene as compound G reacts with the alkylene oxide polymer chain P via its —Cl functions (functions $F^1$) in the allylic position according to a polycondensation (step b)) and it also comprises a post-polymerizable function $F^2$ of alkenyl type.

The post-polymerizable function $F^2$ may be chemically, thermally or photochemically polymerizable, and preferably photochemically polymerizable.

The post-polymerizable functions $F^2$ may be alkoxysilane, alkenyl, alkynyl, vinyl ether, acrylate or methacrylate functions.

When compound G comprises a post-polymerizable function $F^2$, the process of the invention may also comprise a step c) of post-polymerization (e.g. radical polymerization, ionic polymerization or hydrolysis-polycondensation) of the ionomer obtained on conclusion of step b).

The post-polymerization c) (i.e. crosslinking) may make it possible to form a crosslinked ionomer, i.e. a three-dimensional network that is favourable for achieving a cation transport number close to 1.

In the crosslinked ionomer, chemical bonds are formed in all the directions of space so as to lead to the formation of a three-dimensional network.

The post-polymerization step c) may increase the dielectric constant of the ionomer and thus increase the dissociation of the ion pairs of the ionomer.

In particular, an ionomer bearing an alkenyl function may be obtained on conclusion of step b). Next, the ionomer obtained may react with an unsaturated cyclic carbonate such as vinylene carbonate in a step b'). Finally, the ionomer obtained on conclusion of b') may undergo a step c) of post-polymerization (e.g. radical, thermal or photochemical initiation) so as to allow copolymerization between vinylene carbonate and the alkenyl functions of the ionomer.

According to a second variant of the process of the invention, the process may also comprise, after step $a_1$), or optionally after any one of steps $a_i$), a'), $A_i$), A'), α) or α') if it exists, at least one step d) of placing the ionomer in contact with a compound H comprising a function $F^1$ that is capable of condensing with said ionomer and optionally at least one post-polymerizable function $F^2$.

The functions $F^1$ and $F^2$ are as defined previously.

Step d) is consequently a step of condensation of the ionomer with compound H. It makes it possible especially to give the ionomer of formula (III-f) or (III-f') as defined below.

By way of example, compound H comprising a function $F^1$ may be an isocyanatopropyltrialkoxysilane or any other compound comprising only one function $F^1$ that is capable of reacting with the alkylene oxide polymer chain of the ionomer of step $a_1$), or optionally of any one of steps $a_i$), a'), $A_i$), A'), α) or α') if it exists, and especially with the end groups of said chain, according to a polycondensation.

When the compound H is an isocyanatopropyl trialkoxysilane, it may be condensed with alkylene oxide polymer chain P to give a single urethane or urea bond.

When compound H comprises a post-polymerizable function $F^2$, the process of the invention may also comprise a step e) of post-polymerization (e.g. radical polymerization, ionic polymerization or hydrolysis-polycondensation) of the ionomer obtained on conclusion of step d).

In particular, when compound H is an isocyanatopropyl trialkoxysilane, the monomer obtained on conclusion of condensation step d) may undergo a step e) of hydrolysis-polycondensation via a sol-gel method so as to form a polysiloxane.

According to a third variant of the process of the invention, the process may also comprise, after step $a_1$), or optionally after any one of steps $a_i$), a'), $A_i$), A'), α) or α') if it exists, at least one step f) of placing the ionomer in contact with a compound J that is capable of reacting with said ionomer according to a radical or ionic polymerization, and preferably radical polymerization.

Compound J may be chosen from styrene, α-methylstyrene, vinylpyridine, acenaphthylene, acrylic acid, methacrylic acid, an alkyl acrylate (e.g. methyl acrylate), an alkyl methacrylate (e.g. methyl methacrylate), acrylonitrile, methacrylonitrile, an N-alkylacrylamide, an N-alkyl-methacrylamide or vinylene carbonate. Specifically, the hydroxyl (—OH) or primary amine (—$NH_2$) end groups of the alkylene oxide polymer chain may be used to initiate a polymerization giving access to diblock or triblock polymers based on polystyrene, poly-α-methylstyrene, polyvinylpyridine, polyacenaphthylene, polyalkyl acrylate, polyalkyl methacrylate, polyacrylonitrile or polymethacrylonitrile.

Step f) makes it possible especially to give the ionomer of formula (III-g) as defined below.

By way of example, the hydroxyl end groups (—OH) may be converted into sodium alkoxide by treatment with NaH. These alkoxide groups may then initiate the anionic polymerization of acrylonitrile, methacrylonitrile or the alkyl acrylates and methacrylates.

The amine end groups may be converted into sodium amide by treatment with Na metal. These amide groups may then initiate the polymerization of the styrenes.

It is also possible to prepare a polymer of polyether sulfone or polyether ether ketone type terminating, respectively, with a diphenyl sulfone group bearing a terminal chlorine or with a benzophenone group bearing a terminal fluorine. Separately, the ionomer terminating with an —OH or with an —$NH_2$ is converted, respectively, into sodium alkoxide or amide, and then reacts with the terminal chlorine or fluorine of the polymer prepared previously to form a diblock or triblock copolymer.

It is also possible, via controlled differential stoichiometry, to prepare a polyether sulfone or a polyether ether ketone terminated at the two ends, respectively, with chlorines or fluorines. Polycondensation with the ionomers in sodium dialkoxide or diamide form then leads to a polymer with alternating rigid and hydrophobic polyether sulfone and/or polyether ether ketone polymer blocks and flexible and hydrophilic ionomer blocks, the first blocks ensuring excellent mechanical strength and the second the ion-conducting properties. By modifying the size of the rigid blocks, these di-, tri- and multi-block copolymers may be used without adding solvent. The resulting polymers will have noteworthy mechanical properties, but will be less conductive than ionomers based exclusively on polyethers. However, these block copolymers will be highly suited to the formation of gels, the rigid and hydrophobic blocks ensuring excellent mechanical strength and preventing excessive swelling by liquid solvents (e.g. carbonate solvents).

The process may also comprise, after any one of the steps $a_1$), $a_i$), a'), $A_i$), A'), α), α'), b), b'), c), d), e) or f), a step g) of cationic exchange so as to replace the cation M of the ionomer with another desired cation M.

The ionomers of the invention are water-soluble, and are consequently readily purifiable by ultrafiltration in a step h) subsequent of any one of the steps $a_1$), $a_i$), a'), $A_i$), A'), α), α'), b), b'), c), d), e), f) or g).

The difluoro ionic monomer (I) as defined in the invention may be prepared according to a process comprising at least one step i) of reacting a compound (I-a) with a compound (I-b) according to the following reaction scheme:

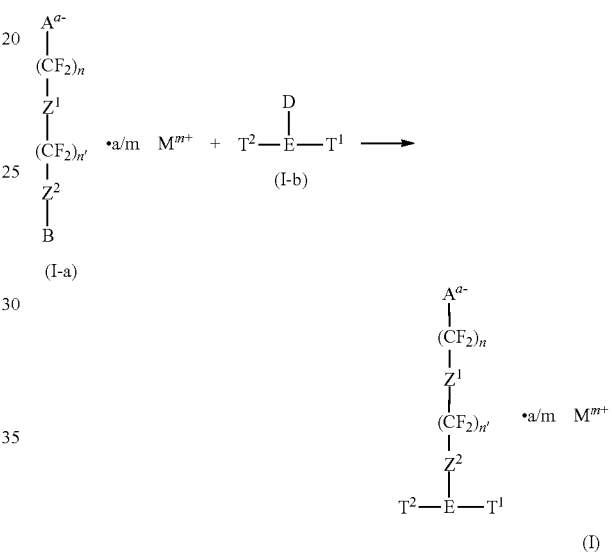

or at least one step i') of reacting a compound (I'-a) with a compound (I'-b) according to the following reaction scheme:

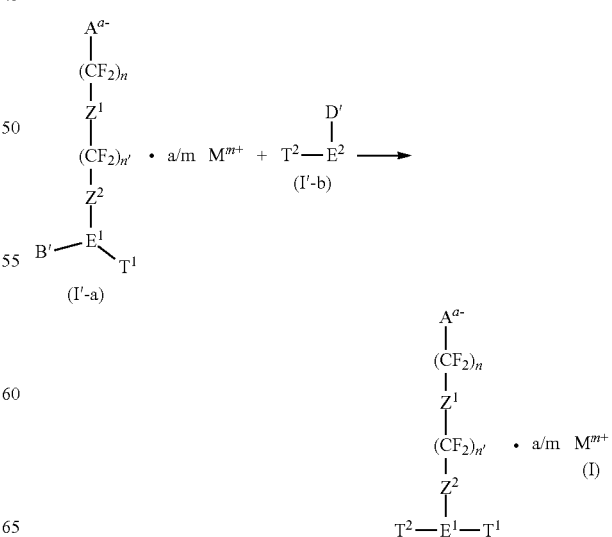

or at least one step i") of reacting a compound (I"-a) with a compound (I"-b) according to the following reaction scheme:

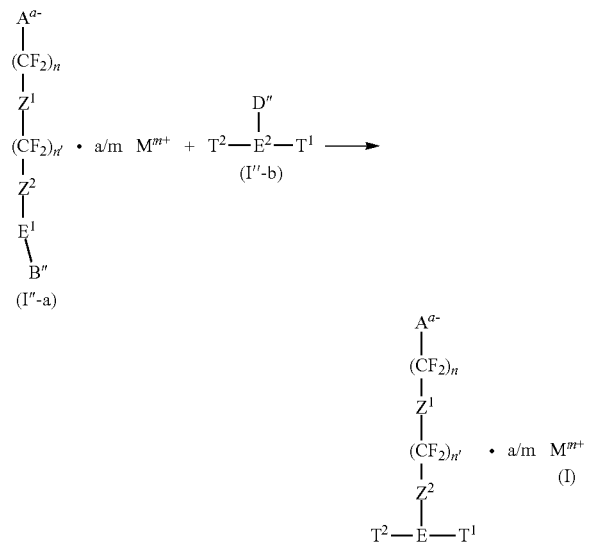

with $Z^1$, $Z^2$, n, n', $T^1$, $T^2$, E, A, a, m and M being as defined in the invention, and the groups B and D, the groups B' and D' and the groups B" and D" being chosen appropriately so as to be able to react together and $E^1$ and $E^2$ being chosen appropriately so as to be able to form the aromatic group E.

Step i) is generally used when E comprises an aromatic ring, whereas step i') or step i") is preferred when E comprises two or three aromatic rings. In addition, if $T^1$ and $T^2$ are not on the same aromatic ring, step i') is used and if $T^1$ and $T^2$ are on the same aromatic ring, step i") is used.

When $Z^2$ is an oxygen atom, step i) is preferably a nucleophilic substitution reaction.

In particular, step i) is performed in the presence of the compound of formula (I-b) in which D is an iodine, bromine or chlorine atom, of the compound of formula (I-a) in which B is a hydrogen atom, and of at least one reagent (base) chosen from sodium carbonate, potassium carbonate, lithium carbonate, sodium hydride, potassium hydride and lithium hydride.

When $Z^2$ is a sulfur atom, step i) is preferably a nucleophilic substitution reaction.

In particular, step i) is performed in the presence of the compound of formula (I-b) in which D is an iodine, bromine or chlorine atom, of the compound of formula (I-a) in which B is a hydrogen atom, and of at least one reagent (base) such as sodium hydride or lithium hydride.

When $Z^2$ is a group S=O or a group $S(=O)_2$, step i) preferably comprises a first substep for gaining access to the difluoro ionic monomer in which $Z^2$ is a sulfur atom, said substep being as defined previously, and a second substep of oxidation.

In particular, step i) is performed according to a first substep in the presence of the compound of formula (I-b) in which D is an iodine, bromine or chlorine atom, of the compound of formula (I-a) in which B is a hydrogen atom, and of at least one reagent (base) such as sodium hydride, lithium hydride, sodium carbonate, potassium carbonate or lithium carbonate, and according to a second substep in the presence of at least one organic peroxide such as meta-chloroperoxybenzoic acid (mCPBA).

The reactions as described above for $Z^2$=O, S, S=O or $S(=O)_2$ are also applicable when n'=0 (and consequently $Z^2$ is a single bond) and $Z^1$=O, S, S=O or $S(=O)_2$.

When $Z^2$ is a C=O group, step i) is preferably a Friedel-Crafts reaction.

In particular, step i) is performed in the presence of the compound of formula (I-a) in which B is a chlorine atom, of the compound formula (I-b) in which D is a hydrogen atom positioned directly on an aromatic ring of the group E and said aromatic ring having in a position ortho to the hydrogen a fluorine atom ($T^1$ or $T^2$) or a methoxy group (—OMe), and reagents of $AlCl_3$ type.

When $Z^2$ is a single bond and n'≠0, or when $Z^1$ is a single bond and n'=0 (and consequently $Z^2$ is a single bond), step i) is preferably a coupling reaction of Ullmann type.

In particular, step i) is performed in the presence of the compound of formula (I-a) in which B is a halogen atom such as an iodine atom, of the compound of formula (I-b) in which D is a halogen atom such as a bromine or iodine atom, and of copper(0) in a solvent such as dimethyl sulfoxide (DMSO) or dimethylacetamide (DMAc).

The process may also comprise a step $i_0$) prior to step i) of preparation of the compound of formula (I-a) from the compound corresponding to formula (I-c) below:

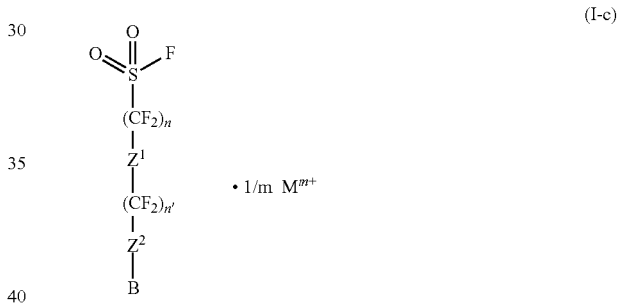

in which $Z^1$, n, m and M are as defined in the invention, $Z^2$ is a single bond and n'≠0 or $Z^1$ is a single bond and n'=0, and the group B is a halogen atom such as an iodine atom.

According to a first variant of step $i_0$), compound (I-c) is placed in contact with a hydroxide of a metal M in an organic solvent such as tetrahydrofuran, M being as defined in the invention. Consequently, hydrolysis of the sulfonyl fluoride (i.e. of compound (I-c)) leads directly to the compound of formula (I-a) in which $A^{a-}$ is a sulfonate anion as defined in the invention.

According to a second variant of step $i_{10}$), compound (I-c) is placed in contact with a sulfonamide of formula $RSO_2NH_2$ in basic medium, especially in the presence of triethylamine, in an organic solvent such as acetonitrile, R being as defined in the invention; and the compound obtained is then placed in contact with a hydroxide of a metal M in aqueous medium, M being as defined in the invention. Consequently, the nucleophilic substitution reaction of the sulfonyl fluoride (i.e. of compound (I-c)) with a sulfonamide of formula $RSO_2NH_2$ and then the formation of the sulfonimide, lead directly to the compound of formula (I-a) in which $A^{a-}$ is a sulfonimide anion as defined in the invention.

According to a third variant of step $i_0$), compound (I-c) is placed in contact with a salt of formula $M'^+(CHR'R")^-$ in an organic solvent such as acetonitrile, $M'^+$ being a monovalent cation such as Na⁺, K⁺ or Li⁺, and R' and R" being as defined in the invention; the compound obtained is then placed in contact with a hydroxide of a metal M in aqueous medium, M being as defined in the invention. Consequently, the nucleophilic substitution reaction of the sulfonyl fluoride (i.e. of compound (I-c)) with a salt of formula $M'^+$ $(CHR'R'')^-$ and then the formation of the carbanion lead directly to the compound of formula (I-a) in which $A^{a-}$ is a carbanion as defined in the invention.

Step i') [or, respectively, step i")] may be performed via a nucleophilic substitution reaction, especially in basic medium, of a compound of formula (I'-b) [or, respectively, of formula (I"-b)] in which D' [or, respectively, D"] is a halogen atom such as a fluorine, chlorine or iodine atom, with a compound of formula (I'-a) [or, respectively, of formula (I"-a)] in which B' [or, respectively, B"] is chosen from a thiol group, an alcohol group, a carboxylic acid group, an amide group and an amine group.

The definitions of B' and D' or B" and D" may be inverted, i.e. step i') [or, respectively, step i")] may be performed via a nucleophilic substitution reaction, especially in basic medium, of a compound of formula (I'-a) [or, respectively, of formula (I"-a)] in which B' [or, respectively, B"] is a halogen atom such as a fluorine, chlorine or iodine atom, with a compound of formula (I'-b) [or, respectively, of formula (I"-b)] in which D' [or, respectively, D"] is chosen from a thiol group, an alcohol group, a carboxylic acid group, an amide group and an amine group.

According to these embodiments, the aromatic group E obtained comprises at least one functional component which allows the aromatic groups $E^1$ and $E^2$ to be connected.

$E^1$ (or, respectively, $E^2$) is an aromatic group comprising from 5 to 15 carbon atoms, and preferably from 5 to 10 carbon atoms, it being understood that $E^1$ (or, respectively, $E^2$) comprises at least one aromatic ring and not more than two aromatic rings.

The aromatic group $E^1$ (or, respectively, $E^2$) may comprise non-aromatic components (known as "functional" components) present on one or more of the aromatic rings or allowing several aromatic rings to be connected together. These non-aromatic components may be alkyl, alkenyl, alkynyl, haloalkyl, conjugated dienyl, alcohol, ether, carboxylic acid, ketone, ester, amide, amine, nitro, etc. groups.

The aromatic group $E^1$ (or, respectively, $E^2$) may comprise heteroatoms such as one or more nitrogen, sulfur or oxygen atoms, or may be constituted solely of carbon and hydrogen atoms.

The term "aromatic ring" is as defined in the invention.

According to a preferred embodiment, $E^1$ and $E^2$ are phenyl groups.

When the group B' or D' [or, respectively, B" or D"] is a thiol group, the process may comprise after step i') or step i"), a step of oxidation of the thiol group to a sulfoxide or to a sulfone.

The process may also comprise before step i'), a step $i_0$') of preparing compound (I'-a) by reacting compound (I-a) as defined previously with a compound (I'-d) having the following formula:

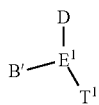

(I'-d)

in which B', D, $E^1$ and $T^1$ are as defined in the present invention.

Step $i_0$') may be performed according to any of the abovementioned reactions in the present invention and which makes it possible to react the group B with the group D, especially according to the nature of $Z^2$ or of $Z^1$ and the value of n' in compound (I-a).

Compound (I-a) may be obtained from compound (I-c) as defined in the present invention, according to one of the variants as described in the present invention. The variant used will be chosen especially as a function of the nature of the desired anion $A^{a-}$.

The process may also comprise before step i"), a step $i_0$") of preparing compound (I"-a) by reacting compound (I-a) as defined previously with a compound (I"-d) having the following formula:

in which B", D and $E^1$ are as defined in the present invention.

Step $i_0$") may be performed according to any of the abovementioned reactions in the present invention and which makes it possible to react the group B with the group D, and especially according to the nature of $Z^2$ or of $Z^1$ and the value of n' in compound (I-a).

Compound (I-a) may be obtained from compound (I-c) as defined in the present invention, according to one of the variants as described in the present invention. The variant used will be chosen especially as a function of the nature of the desired anion $A^{a-}$.

Thus, the process for preparing the difluoro ionic monomers (I) is simple and economical. In particular, the presence of the two fluorine atoms as groups $T^1$ and $T^2$ is advantageous since it makes it possible rapidly and quantitatively to obtain the difluoro ionic monomers (I). Specifically, firstly, the difluoro ionic monomers obtained are readily purifiable, and, secondly, the process avoids all the protection and deprotection steps that would be necessary if groups such as hydroxyl, amine, carboxylic acid, ester or thiol were used in place of the fluorine atoms $T^1$ and $T^2$ of the invention.

Moreover, the difluoro ionic monomers (I) have the advantage of reacting with alkylene oxide oligomers or polymers by forming ether bonds that are more stable, especially with respect to hydrolysis, than ester and amide bonds that would be obtained if the starting materials were ionic monomers difunctionalized with carboxylic acid or ester groups. This better stability allows washing with water without degradation of said difluoro ionic monomer (I).

A second subject of the invention is an ionomer, characterized in that it comprises at least repeating units UP corresponding to formula (II) below:

(II)

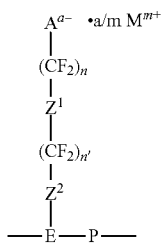

in which A, n, n', $Z^1$, $Z^2$, E, m, a and M are as defined in the first subject of the invention, and P is an alkylene oxide polymer chain.

P is as defined in the first subject of the invention.

The ionomer may comprise p units UP, preferably at least two units UP, especially with $2 \leq p \leq 100$, and preferably $2 \leq p \leq 50$.

The ionomer may be obtained according to the process in accordance with the first subject of the invention.

As explained above, the process of the invention is a polycondensation which makes it possible to form repeating units UP as defined above or, in other words, an ionomer containing an alternation of: ionic group $E-Z^2-(CF_2)_{n'}-Z^1-(CF_2)_n-A^{a-}.(a/m)\ M^{m+}$/alkylene oxide polymer chain/ionic group $E-Z^2-(CF_2)_{n'}-Z^1-(CF_2)_n-A^{a-}.(a/m)\ M^{m+}$/alkylene oxide polymer chain, etc. Such an alternation makes it possible to avoid the presence of adjacent ionic groups which decreases the dissociation and, consequently, the ion conductivity of the polymer obtained. Polycondensation also makes it possible to obtain an ionomer in which the position of the ionic groups is precisely known.

In a particularly preferred embodiment of the invention, the alkylene oxide polymer chain P of the ionomer is bonded directly to the aromatic ring(s) of the group E (via the end groups of the alkylene oxide polymer $P^1$ or terminal heteroatoms of the alkylene oxide polymer chain). This ionomer is obtained via the process of the invention when the fluorine atoms $T^1$ and $T^2$ are substituents of aromatic ring(s) of the aromatic group E.

In a particular embodiment, the ionomer comprises only repeating units UP.

It thus corresponds to formula (III-a) below:

(III-a)

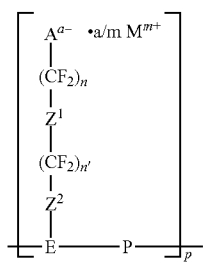

in which A, n, n', $Z^1$, $Z^2$, E, m, a, M, P and p are as defined in the first subject of the invention.

According to a preferred embodiment of the invention, the ionomer of the invention corresponds to any one of the formulae (III-a') below:

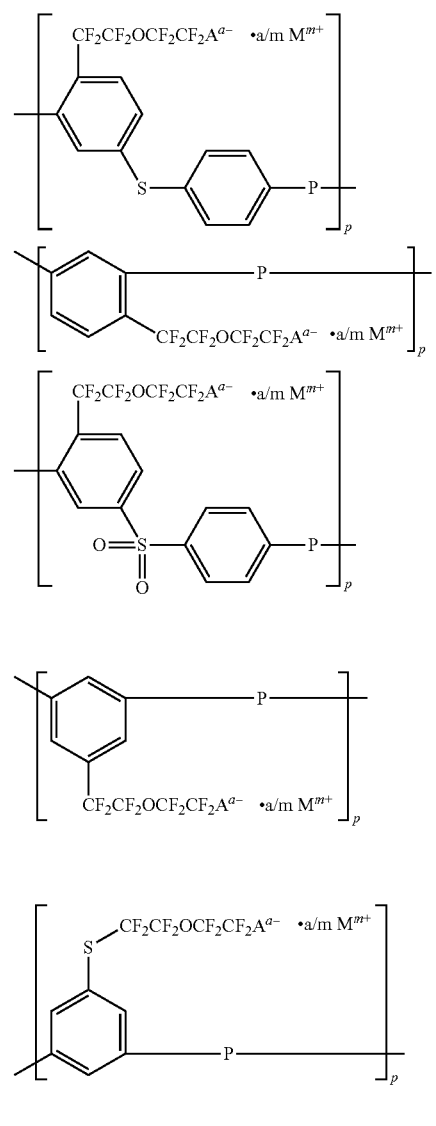

in which A, m, a, M, P and p are as defined in the first subject of the invention.

In another embodiment, the ionomer also comprises alkylene oxide polymer chains P' having the same definition as that of the alkylene oxide polymer chains P, with P' being different from P.

In this case, the ionomer may correspond to formula (III-$b_1$), (III-$c_1$) or (III-$d_1$) below:

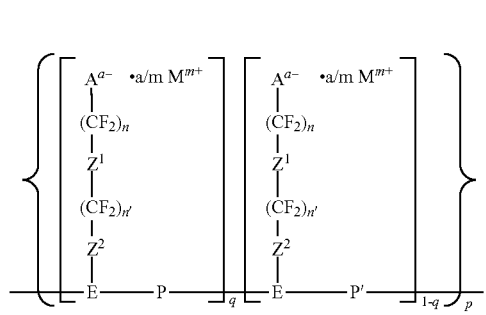

(III-b₁)

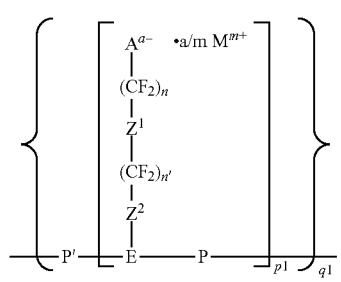

(III-d₁)

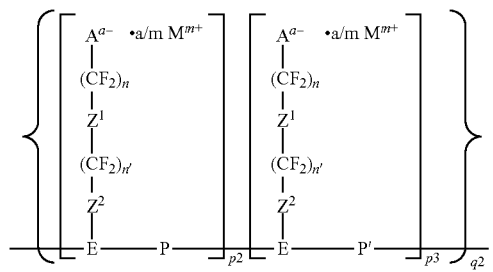

(III-c₁)

in which A, n, n', $Z^1$, $Z^2$, E, m, a, M, P, P' and p are as defined in the first subject of the invention, q, $q_1$, $q_2$, $p_1$, $p_2$ and $p_3$ have the same definition as p.

In another embodiment, the ionomer also comprises difluoro ionic monomers (I') having the same definition as that of the difluoro ionic monomers (I), with the monomers being different.

In this case, the ionomer may correspond to formula (III-b₂), (III-c₂) or (III-d₂) below:

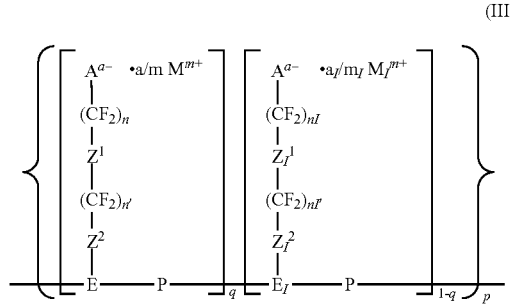

(III-b₂)

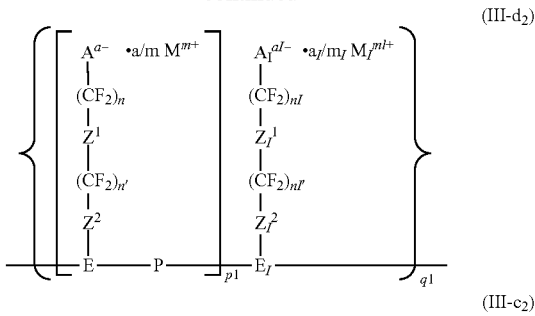

(III-d₂)

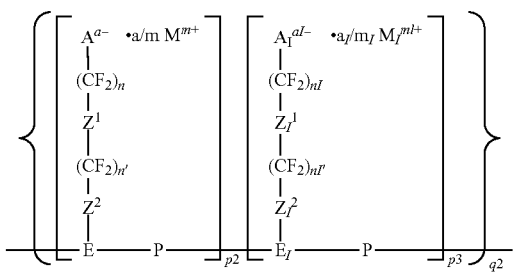

(III-c₂)

in which A, n, n', $Z^1$, $Z^2$, E, m, a, M, P and p are as defined in the first subject of the invention, q, $q_1$, $q_2$, $p_1$, $p_2$ and $p_3$ have the same definition as p, and $A_I$, $n_I$, $n_I'$, $Z_I^1$, $Z_I^2$, $E_I$, $m_I$, $a_I$ and $M_I$ have, respectively, the same definition as A, n, n', $Z^1$, $Z^2$, E, m, a and M, it being understood that $A_I$ is different from A and/or $n_I$ is different from n and/or $n_I'$ is different from n' and/or $Z_I^1$ is different from $Z^1$ and/or $Z_I^2$ is different from $Z^2$ and/or $E_I$ is different from E and/or $M_I$ is different from M.

In a particular embodiment, the ionic parts differ only by the anion (i.e. $A_I^{aI-}$ different only from $A^{a-}$). For example, $A^{a-}$ may be a sulfonate anion and $A_I^{aI-}$ a sulfonimide anion.

The alkylene oxide polymer chain P may be polycondensed by means of its end groups, with a compound G as defined in the third subject of the invention (cf. 1ˢᵗ variant of the process of the invention).

In this case, the ionomer of the invention may correspond to formula (III-e) below:

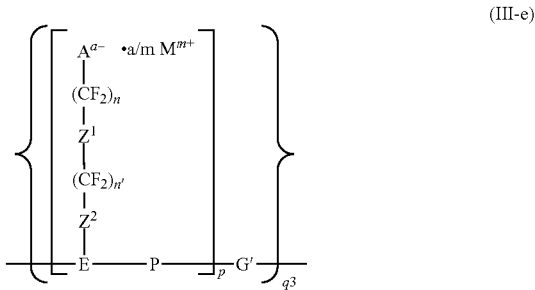

(III-e)

in which A, n, n', $Z^1$, $Z^2$, E, m, a, M, P and p are as defined in the first subject of the invention, $q_3$ has the same definition as p, and G' results from polycondensation of compound G with the end groups of P.

For example, when a compound G is a diisocyanate $Ph(NCO)_2Me$ (toluene diisocyanate), the ionomer obtained may correspond to formula (III-e') below:

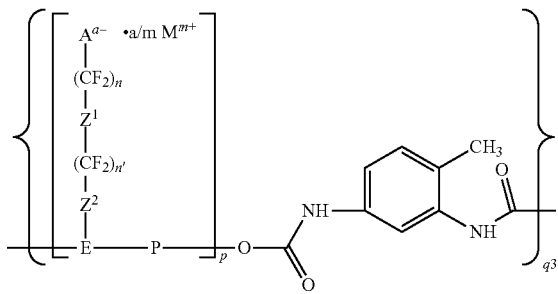

in which A, n, n', $Z^1$, $Z^2$, E, m, a, M, P and p are as defined in the first subject of the invention, and $q_3$ has the same definition as p.

In this example, toluene diisocyanate is polycondensed with the alkylene oxide polymer chain P via its alcohol end groups to form urethane bridges.

When compound G comprises a post-polymerizable function $F^2$ as defined in the third subject of the invention, a crosslinked ionomer may be obtained, i.e. chemical bonds are formed in all directions of space so as to lead to the formation of a three-dimensional network.

In another embodiment, the alkylene oxide polymer chain P may be condensed by means of its end groups, with a compound H as defined in the third subject of the invention (cf. $2^{nd}$ variant of the process of the invention).

In this case, the ionomer obtained is functionalized at the end of the chain with compound H and the ionomer corresponds to formula (III-f) below:

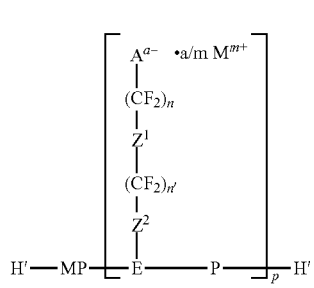

(III-f)

in which A, n, n', $Z^1$, $Z^2$, E, m, a, M, P and p are as defined in the first subject of the invention, MP corresponds to the monomer of the polymer chain P, and H' results from polycondensation of compound H with the end groups of the polymer chain P.

For example, when a compound H is an isocyanatopropyltriethoxysilane of formula $(EtO)_3Si(CH_2)_3(NCO)$, the ionomer obtained may correspond to formula (III-f') below:

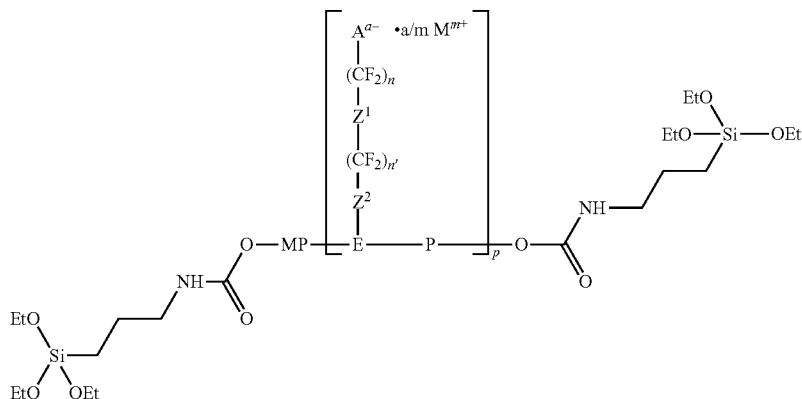

in which A, n, n', $Z^1$, $Z^2$, E, m, a, M, P and p are as defined in the first subject of the invention, and MP corresponds to the monomer of the polymer chain P.

In this example, the isocyanate is condensed with an ionomer via its alcohol end groups to form urethane bridges. The ionomer obtained is functionalized at the end of the chain with compound H and comprises repeating units UP (p units).

In another embodiment, the end groups, especially the alcohol (OH) or primary amine ($NH_2$) groups, of the alkylene oxide polymer chain P may be used to initiate a polymerization for gaining access to diblock or triblock polymers, especially based on polystyrene, poly-α-methylstyrene, polyvinylpyridine, polyacenaphthylene, polyacrylate, polymethacrylate, polyacrylonitrile or polymethacrylonitrile (cf. $3^{rd}$ variant of the process of the invention).

In this case, the ionomer may correspond to formula (III-g) below:

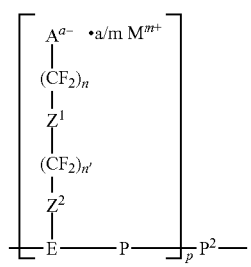

(III-g)

in which A, n, n', $Z^1$, $Z^2$, E, m, a, M, P and p are as defined in the first subject of the invention, and $P^2$ is a polymer chosen from a polystyrene, a poly-α-methylstyrene, a polyvinylpyridine, a polyacenaphthylene, a polyacrylate, a polymethacrylate, a polyacrylonitrile and a polymethacrylonitrile.

The ionomers of the invention have great capacity for dissociation in aprotic medium.

Preferably, they have a unipolar ion conductivity of greater than or equal to $10^{-6}$ S·cm$^{-1}$ at room temperature, and preferably greater than or equal to $10^{-5}$ S·cm$^{-1}$ at room temperature.

The ionomer of the invention may have a glass transition temperature $T_g$ of less than or equal to about −20° C., and preferably less than or equal to about −40° C.

The ionic functions of the ionomer of the invention are chosen so as to optimize the dissociation in aprotic medium, while at the same time disrupting the crystallization of the polyalkylene oxide-based polymer matrix so as to optimize the conductivity at room temperature.

The ionomer of the invention preferably has an average molar mass $M_w$ (mass-average molar mass) ranging from 1000 g/mol to 300 000 g/mol approximately, and more preferably from 20 000 g/mol to 300 000 g/mol approximately.

In a particular embodiment, the ionomer has a cation transport number of greater than or equal to about 0.9, and preferably equal to 1.

In the ionomer of the invention, only the cations $M^{m+}$ transport the current when it is used in an electrochemical device.

The ionomer may reach an ion transport number close to 1 due to the immobility of the anions $A^{a-}$, obtained by means of grafting of said anions in a three-dimensional network or onto long chains of one-dimensional polymer whose lengths are largely superior to the entanglement threshold.

The ionomer of the invention may also comprise postpolymerizable functions for obtaining a solvating polymer with three-dimensional cationic conduction (crosslinked ionomer). Such a crosslinked ionomer may have a storage modulus ranging from 1 to 5 MPa approximately, and preferably ranging from 3 to 5 MPa approximately.

A third subject of the invention is an electrolytic composition, characterized in that it comprises at least one ionomer in accordance with the second subject of the present invention or obtained according to the process in accordance with the first subject of the present invention.

The electrolytic composition may be constituted solely of the ionomer of the invention.

The electrolytic composition may also comprise one or more organic solvents, chosen especially from carbonates (e.g. mixtures of propylene carbonate, ethylene carbonate and dimethyl carbonate in variable proportions), N-methylacetamide, γ-butyrolactone, dimethylformamide, N-methylpyrrolidone, tetraalkylsulfamides, an ionic liquid based on quaternary ammonium, and polyethylene glycol dimethyl ethers with a mass of between 90 and 2000.

The organic solvent(s) exert: 1) a dissociating effect due to their high dielectric constant, and 2) a plasticizing effect which promotes the mobility of the cation M.

The amount of organic solvents is preferably less than 70% by mass, preferably between 25% and 50% by mass. A gelled polymeric electrolyte is then obtained. In this case, the ionomer will have to comprise a high content of ionic function, i.e. with polyether spacers not exceeding 400 g/mol. Preferably, an ionomer of block copolymer type will be used to ensure a good mechanical property.

The electrolytic composition may also comprise one or more additives chosen from mineral fillers, alkali metal salts such as the lithium salts conventionally used in liquid electrolytes (e.g. LiTFSI, LiClO$_4$ or LiPF$_6$), organic fillers such as cellulose-based organic fillers, complexing agents, flame retardants, and a mixture thereof.

The complexing agent is specific for the cation M as defined in the invention and can promote the dissociation of the ion pairs and increase the mobility of the cation M. This complexing agent, which depends on the nature of the cation M, may be a crown ether or a cyclam, and may be solid or liquid.

In the case of lithium ionomers, tetramethyltetraazacyclotetradecane (solid) or liquid sparteine, which boils at very high temperature, may be used.

The mineral filler may be silica.

The cellulose-based organic filler may be chosen from cellulose fibres, cellulose nanofibres and cellulose microfibrils, said fibres, nanofibres or microfibrils being optionally functionalized with groups such as sulfonate —SO$_3^-$ or sulfate ester —O—SO$_3^-$.

According to one embodiment of the invention, the electrolytic composition does not comprise any solvent and preferably comprises not more than 10% by mass approximately of alkali metal salt(s) (e.g. lithium salt). A "solvent-free" electrolytic composition comprising small mass concentrations of salt is thus obtained. This electrolytic composition has the advantage of having improved conductivity. The cation transport number will, admittedly, be decreased, but the presence of the ionomer will counter the creation of a salt concentration gradient.

The electrolytic composition may also comprise one or more nonionic polymers such as poly(oxyethylene).

This embodiment is particularly advantageous for manufacturing composite electrodes in which the electrolytic composition acts as binder.

In the electrolytic composition, the ionomer may be used in its saturated polycondensate form, in its unsaturated polycondensate form or in the form of block copolymers comprising the saturated polycondensate.

The electrolytic composition may be formed by hot pressing, by extrusion or by coating a substrate to give an electrolyte in the form of a film, especially when the electrolytic composition comprises a cellulose-based organic filler.

When an electrolytic composition according to the invention is prepared in the form of a film or in the form of a gelled polymeric electrolyte, it is directly usable as electrolytic film or gelled polymeric electrolyte for an electrochemical device.

When it is desired to form a film, the preparation of the electrolytic film may comprise the preparation of a solution of an ionomer of the invention, and optionally of one or more organic solvents and/or of one or more additives in a volatile solvent, degassing of the solution obtained, and then a step in which said solution is poured onto a substrate, and drying of the film under vacuum by evaporation of the solvent.

As volatile solvent, mention may be made, for example, of water, acetonitrile, dimethylformamide or dichloromethane. A substrate whose surface is coated with a layer of an inert and non-stick material such as polytetrafluoroethylene is preferably used. The surface of the cast film may be delimited by a glass ring bonded onto the surface of the substrate.

When the ionomer comprises post-crosslinkable double bonds (functions $F^2$), it is advantageously possible to add to an aqueous solution of the ionomer a thermal initiator or a radical photoinitiator that is water-soluble, cast the film, dry it and then crosslink it either by heat (thermal initiation) or by UV irradiation (photoinitiator).

Water-based manufacturing processes are highly favoured by battery manufacturers.

When the crosslinked or non-crosslinked ionomer is intended to be reinforced with organic fillers of cellulose type, these fillers may be dispersed in the aqueous ionomer solution (e.g. obtained after ultrafiltration) optionally in the presence of a thermal initiator or of a radical photoinitiator that is water-soluble, cast the film, dry it and then optionally crosslink it. A film reinforced with organic fillers of cellulose type is thus obtained, which is directly usable in an electrochemical device such as a battery.

When it is desired to manufacture a composite electrode using the electrolytic composition of the invention as binder, an ink comprising the active material should be prepared (e.g. LFP for the positive electrode and graphite or LTO for the negative electrode), the electrolytic composition comprising at least one ionomer and one or more nonionic polymers, and carbon such as carbon black or carbon nanotubes.

The active material may also be an organic active material such as a redox organic polymer (e.g. poly(phenothiazine) or PPT) or an organic/inorganic mixed active material such as a PPT/LFP mixture.

When the polycondensate is unsaturated, the ink also comprises an initiator, with thermal or photochemical (UV) decomposition, to crosslink the ink once it has dried. It is thus possible to separately crosslink the ionomer before the preparation of the ink or to crosslink the ink directly, thus making it possible to improve the active material/electrolytic composition/carbon interfaces within the composite electrode.

A fourth subject of the invention is the use of an ionomer in accordance with the second subject of the present invention or obtained according to the process in accordance with the first subject of the present invention, for the manufacture of an electrolyte, especially in the form of an electrolytic film or of a gelled polymeric electrolyte, for an electrochemical device such as a battery (e.g. lithium, lithium-ion, lithium-sulfur, lithium-air, sodium, sodium-ion, magnesium, calcium or aluminium batteries), a supercapacitor, electrochromic glazing or a solar cell.

A fifth subject of the invention is the use of an ionomer in accordance with the second subject of the present invention or obtained according to the process in accordance with the first subject of the present invention, as ionic liquid.

In this use, the molar mass of the ionomer is less than or equal to 20 000 g/mol approximately, and preferably less than or equal to 2000 g/mol approximately.

Unlike conventional ionic liquids based on quaternary ammonium, the ionic liquids of the invention participate directly in the electrochemical reactions and do not require the addition of a lithium salt (lithium batteries) or a sodium, magnesium or calcium salt (Na, Mg or Ca batteries).

Conventional ionic liquids are very difficult to purify since they are amorphous, liquid at low temperature and can neither be distilled nor sublimed, which makes battery-grade ionic liquids very expensive. By choosing ionic liquids of the invention with a molar mass >1000 g/mol, they can be readily purified by ultrafiltration in water.

The ionomers of the invention as ionic liquids may be used as a mixture with a dense membrane based on polymer of POE type, or with a macroporous membrane of Celgard® or PVdF type. The ionomer used as ionic liquid then fills the pores of the macroporous membrane. If the ionomer is not crosslinked, it will have a cation transport number of about 0.7. Once the pores of the macroporous membrane have been filled with the ionomer, it may be crosslinked to form an ionic polyliquid with a cation transport number equal to 1.

The ionomers of the invention as ionic liquids may also be used as a mixture with neutral polymers of high molar mass such as POE 300 000 to make composite electrodes.

A sixth subject of the invention is the use of an ionomer in accordance with the second subject of the present invention or obtained according to the process in accordance with the first subject of the present invention, to make composite electrodes, i.e. as constituent of a composite electrode, in particular as conductive binder of a composite electrode.

The use of ionomers as electrode binder gives the electrode ion conduction, the composite electrode then having electronic conduction ensured by the conductive agent (e.g. carbon black), ion conduction ensured by the ionomer and an active material. Using ionomers with a chain length which is either very much greater than the entanglement threshold (non-crosslinked ionomer) or infinite (crosslinked ionomer) ensures that the ionomers will not migrate during charging/discharging cycles, thus preventing salt depletion of the composite electrode.

The ionomer of the invention thus has a fourfold function: as macromolecular solvent, as unipolar cation conductor, as separator and as ionic electrode binder.

The ionomer according to the present invention may also be used as constituent of selective membranes or of reference membranes in membrane sensors.

A seventh subject of the invention is an electrochemical device comprising at least one negative electrode and at least one positive electrode separated by an electrolytic composition, characterized in that the electrolytic composition is in accordance with the third subject of the invention.

In a particular embodiment, the positive electrode (or, respectively, the negative electrode) is a composite electrode and it comprises an electrolytic composition in accordance with the fifth subject of the invention, especially as conductive binder.

Such an electrochemical device may be an electrical battery, a supercapacitor, electrochromic glazing or a solar cell, and preferably a lithium, lithium-polymer, lithium-ion, lithium-sulfur, lithium-air, sodium, magnesium or calcium battery.

DETAILED DESCRIPTION

EXAMPLES

Figure 1:
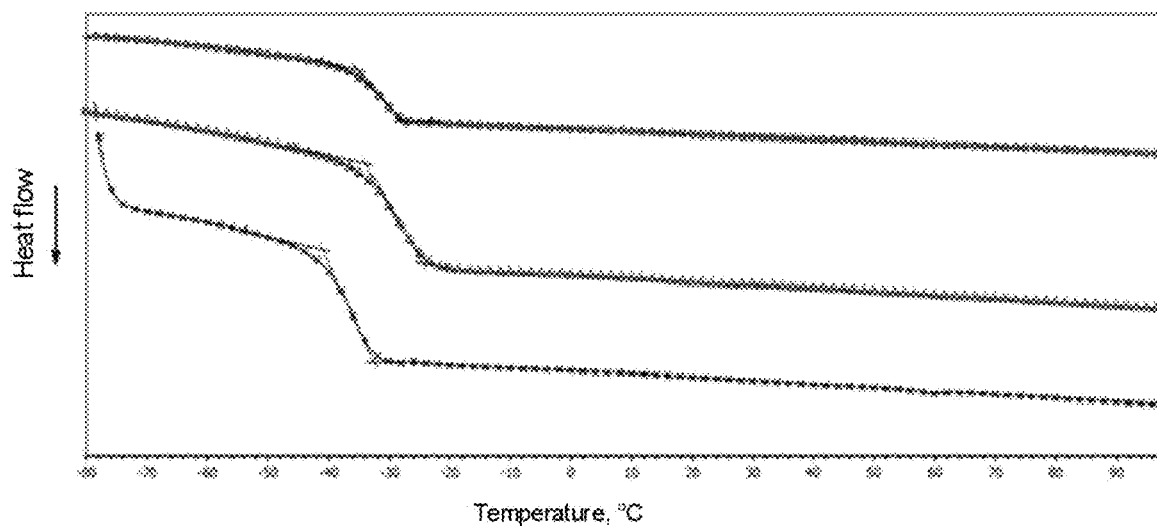
FIG. 1 show DSC analyses showing heat flow as a function of the temperature from example 11, in accordance with one embodiment

Unless otherwise mentioned, all the starting materials of the examples were used as received from the manufacturers.

The materials prepared (e.g. monomers and/or ionomers) were characterized by:

proton and/or fluorine nuclear magnetic resonance (NMR), measurement of the ion conductivity by electrochemical impedance spectrometry, Differential Scanning Calorimetry (DSC), thermomechanical analysis (also known as "*Dynamic Mechanical Analysis*" or DMA), measurement of the cation transport number by low-frequency impedance spectrometry, measurement of the molar mass by size exclusion chromatography using a Waters 515 HPLC coupled to a Wyatt Dawn EOS light-scattering multi-angle detector at 690 nm approximately (also known as "*Size Exclusion Chromatography coupled to Multi-Angle Laser Light Scattering*" or SEC-MALLS).

The fluorine and hydrogen nuclear magnetic resonance analyses were performed using a machine sold under the brand name Avance III HD by the company Bruker, with the following parameters: frequencies 400.15 MHz for proton NMR ($^1$H NMR) and 376.52 MHz for fluorine NMR ($^{19}$F NMR).

The ion conductivity measurements were taken using an HP 4192A impedance meter sold by the company Hewlett Packard and functioning in the frequency range 5 Hz-13 MHz, the sinusoidal signal amplitude being set at ±10 mV. The measurements were taken at a temperature ranging from 20° C. to 90° C. in a thermostatic oven. The measurements were taken every 10° C. after temperature stabilization for 1 hour, especially during the temperature descent. The samples were placed in a glovebox under argon in Swagelok® cells. Each measurement was taken twice so as to ensure reproducibility of the ion conductivities determined.

The differential scanning calorimetry analyses were performed with a machine sold under the trade name DSC 1 STARe system by the company Mettler Toledo. They make it possible to obtain the glass transition temperature of the ionomers obtained.

The thermomechanical analyses (i.e. measurement of the storage modulus) were performed using a machine sold under the trade name DMA Q800 by the company TA instruments (Waters).

Size exclusion chromatography was performed on $C_{18}$ Agilent 2×PLgel-Mixed-D columns using as elution solvent 0.1M sodium nitrate in dimethylformamide. The elution rate of the solvent was 1 ml/min approximately.

The cation transport number was determined by the method described by Sorensen et al. [*Electrochimica Acta*, 1982, 27, 12, 1671-1675] which uses low-frequency electrochemical impedance spectroscopy. This scattering impedance may be represented by a Warburg impedance included in an equivalent electrical circuit. The cation transport number was measured at about 70° C. in a lithium/electrolyte/lithium symmetrical flexible cell of "coffee bag" type.

Example 1

Preparation of a Difluoro Ionic Monomer $M^1$

The synthetic scheme for obtaining the difluoro ionic monomer $M^1$ is as follows:

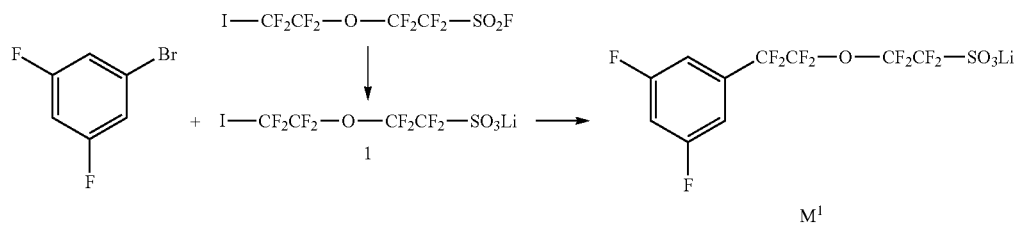
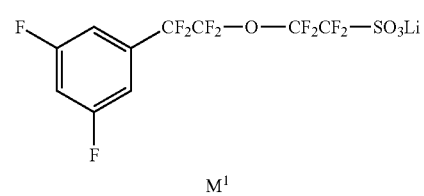

1.1) First Step: Synthesis of Compound 1 (lithium 5-iodooctafluoro-3-oxapentanesulfonate)

Compound 1 was obtained by hydrolysis of 5-iodooctafluoro-3-pentanesulfonyl fluoride in an organic solvent in the presence of LiOH (lithine).

In particular, 10.22 g (0.024 mol) of 5-iodooctafluoro-3-pentanesulfonyl fluoride were dissolved in 48 ml of tetrahydrofuran (THF). Next, 2.22 g (0.053 mol) of lithine were introduced into the THF solution and the resulting reaction medium was maintained under vigorous stirring for 12 hours at room temperature and under an inert atmosphere.

Disappearance of the starting material in the reaction medium (i.e. at the end of the hydrolysis) was monitored and controlled by fluorine NMR ($^{19}$F NMR) analysis by means of the disappearance of the peak at 52 ppm and corresponding to the fluorine in the "SO$_2$F" unit.

The reaction medium was filtered so as to remove the excess lithine and the THF was evaporated off. The residue obtained was dissolved in acetonitrile and then filtered through a filter with a filtration threshold of about 0.2 μm. Compound 1 was obtained in a yield of about 85% in the form of a white powder, after evaporation of the acetonitrile and then drying for 24 hours at 80° C. approximately under reduced pressure. It was stored in the absence of air under an inert atmosphere.

Compound 1 was characterized by fluorine NMR:

$^{19}$F NMR: δ (ppm, acetone-d$_6$)=−118.6 (s, C$\underline{F}_2$SO$_3$Li); −86.52 (m, C$\underline{F}_2$O); −82.95 (t, C$\underline{F}_2$O); −69.06 (s, IC$\underline{F}_2$).

A similar process was used to prepare sodium 5-iodooctafluoro-3-oxapentanesulfonate (98% yield, compound 2) and potassium 5-iodooctafluoro-3-oxapentanesulfonate (98% yield, compound 3).

Compound 3 was characterized by fluorine NMR:

$^{19}$F NMR: δ (ppm, acetone-d$_6$)=−118.6 (s, C$\underline{F}_2$SO$_3$K); −86.52 (m, C$\underline{F}_2$O); −82.94 (t, C$\underline{F}_2$O); −69.10 (s, IC$\underline{F}_2$).

1.2) Second Step: Synthesis of Compound $M^{1'''}$ (potassium 3,5-(difluorophenyl)octafluoro-3-oxapentanesulfonate)

A solution comprising 8.25 g (0.130 mol) of copper(0) and 7.5 ml (0.065 mol) of 1-bromo-3,5-difluorobenzene in 10 ml of distilled dimethyl sulfoxide (DMSO) was prepared. The resulting reaction medium was kept stirring for 1 hour 30 minutes at about 115-120° C.

A solution comprising 15.0 g (0.032 mol) of compound 3 (K⁺ form) in 17 ml of DMSO was prepared separately and then added to the reaction medium. The resulting reaction medium was stirred for 3 hours at about 125° C. and then cooled to room temperature, filtered through Celite®545 so as to remove the excess copper, and poured into 200 ml of saturated aqueous sodium chloride solution (brine). The compound was extracted 3 times with 200 ml of ethyl acetate. Next, the organic phases were combined, washed once with 400 ml of water, dried over $Na_2SO_4$ and filtered, and the solvents were evaporated off. The residue obtained (yellowish solid) was washed with hexane and then with toluene and dichloromethane until the washing solvent was transparent. The monomer $M^{1''}$ was obtained in a yield of about 75%, in the form of a white solid.

The monomer $M^{1''}$ was characterized by fluorine and proton NMR:

$^1H$ NMR: δ (ppm, acetone-$d_6$)=7.34 (t-t, $1H_{Ar}$); 7.50 (d-d, $2H_{Ar}$).

$^{19}F$ NMR: δ (ppm, acetone-$d_6$)=−119.11 (s, $CF_2SO_3K$); −114.34 (t, $CF_2Ar$); −108.70 (t, $2 F_{Ar}$); −88.38 (m, $CF_2O$); −83.48 (m, $CF_2O$).

A similar process was used to prepare the monomer lithium 3,5-(difluorophenyl)octafluoro-3-oxapentanesulfonate (monomer $M^1$) and the monomer sodium 3,5-(difluorophenyl)octafluoro-3-oxapentanesulfonate (monomer $M^{1'}$) in respective yields of 76% and 78%.

Example 2

Preparation of a Difluoro Ionic Monomer $M^2$

The synthetic scheme for obtaining the difluoro ionic monomer $M^2$ is as follows:

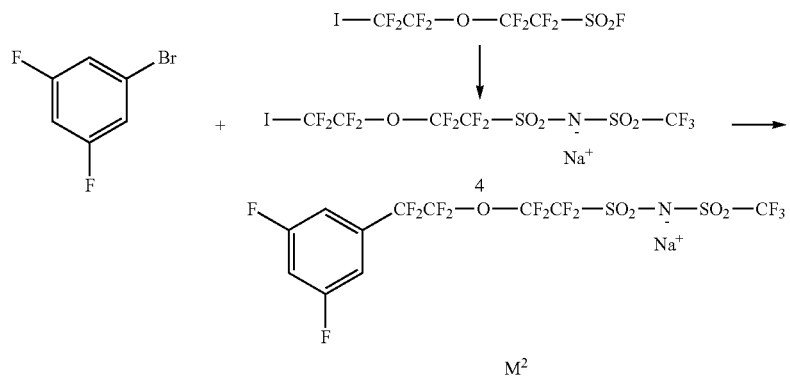

2.1) First Step: Synthesis of Compound 4 (sodium 5-iodooctafluoro-3-oxapentanetrifluoromethanesulfonimide)

25.82 mmol of trifluoromethanesulfonamide and 49.30 mmol of triethylamine were dissolved in 20 ml of acetonitrile (ACN), freshly distilled over calcium hydride, in a two-necked round-bottomed flask, and the resulting mixture was stirred. 23.47 mmol of 5-iodooctafluoro-3-oxapentanesulfonyl fluoride were then added and the resulting mixture was heated at about 40° C. for 36 to 40 hours.

Disappearance of the starting material in the reaction medium (i.e. at the end of the hydrolysis) was monitored and controlled by fluorine NMR ($^{19}F$ NMR) analysis by means of disappearance of the peak at 52 ppm and corresponding to the fluorine in the "$SO_2F$" unit.

The solvent was evaporated off under reduced pressure at about 40° C. The residue obtained was then dissolved in dichloromethane, washed with 1000 ml of distilled water and dried over magnesium sulfate. The solvents were evaporated off under reduced pressure at about 40° C. The residue obtained was then dissolved in aqueous sodium hydroxide (NaOH) solution so as to have a molar excess of NaOH of about 5%. After stirring for 15 minutes, the water was removed by lyophilization. NaOH allowed exchange between ammonium and sodium. A viscous oil was obtained and was then dissolved in acetonitrile, dried over magnesium sulfate and filtered, and the solvents were evaporated off under reduced pressure at about 40° C. The residue obtained was recrystallized from anisole to give compound 4.

2.2) Second Step: synthesis of the monomer $M^2$ (sodium 3,5-(difluoro-phenyl)octafluoro-3-oxapentanetrifluoromethanesulfonimide)

4 equivalents of copper(0) (2.265 g, 35.64 mmol) and 2 equivalents of 1-bromo-2,5-difluorobenzene (3.44 g, 17.82 mmol) were dissolved in 10 ml of undistilled DMSO in a round-bottomed flask equipped with a condenser and a thermometer. The resulting reaction medium was stirred for 1 hour 30 minutes at a temperature ranging from 115 to 120° C. approximately and under inert atmosphere. The temperature was then lowered to about 70° C.

A solution comprising 1 equivalent of compound 4 (5 g, 8.91 mmol) in 7 ml of DMSO was prepared separately and was added to the reaction medium. The temperature of the resulting mixture was brought to about 127° C. At the end of the reaction, the resulting mixture was filtered through Celite®545 to remove the excess copper, and then poured into 200 ml of saturated aqueous sodium chloride solution. The compound was extracted 3 times with 200 ml of ethyl acetate. The organic phases were then combined, dried over $Na_2SO_4$, and filtered, and the solvents were evaporated off. The residue obtained was washed with hexane, then with toluene and dichloromethane until the washing solvent was transparent. The monomer $M^2$ was obtained in a yield of about 70%.

The monomer $M^2$ was characterized by fluorine and carbon NMR:

$^{13}$C NMR: δ (ppm, acetone-d$_6$)=120.7 (q, J=321.5 Hz, C9); 112.8 (tt, J=294.6 Hz, J=34.6 Hz, C6); 117.6 (tt, J=287.5 Hz, J=31.3 Hz, C8); 117.9 (tt, J=287.5 Hz, J=37.1 Hz, C7); 163.9 (dd, J=12.6 Hz, J=250.5 Hz, C2); 132.5 (septet, J=9.8 Hz, C4); 111.4 (dt, J=27.7 Hz, J=7.4 Hz, C3); 108.4 (t, J=24.7 Hz, C1); 113.7 (tt, J=255.4 Hz, J=33.1 Hz, C5).

$^{19}$F NMR: δ (ppm, acetone-d$_6$)=−79.87 (s, 3F, F$_9$); −82.16 (s, 2F, F$_6$); −88.15 (s, 2F, F$_7$); −108.53 (s, 2F, F$_2$); 114.66 (s, 2F, F$_5$); −117.27 (s, 2F, F$_8$).

Example 3

Preparation of a Difluoro Ionic Monomer M$^3$

The synthetic scheme for obtaining the difluoro ionic monomer M$^3$ is as follows:

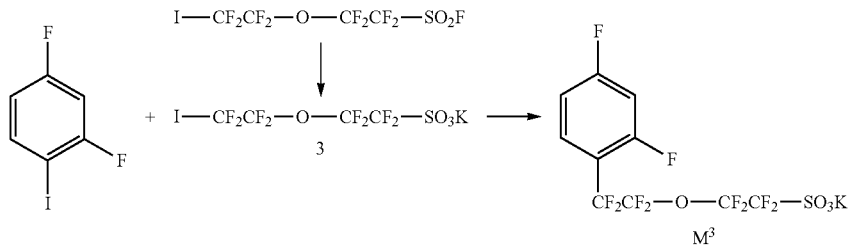

3.1) First Step: Synthesis of Compound 3 (potassium 5-iodooctafluoro-3-oxapentanesulfonate)

Compound 3 was obtained by hydrolysis of 5-iodoocta-fluoro-3-pentanesulfonyl fluoride in an organic solvent in the presence of KOH according to the process as described in Example 1.1).

3.2) Second Step: Synthesis of Compound M$^3$ (potassium (2,4-difluoro-phenyl)octafluoro-3-oxapentanesulfonate)

1.0 g of 2,4-difluoro-1-iodobenzene (4.08 mmol), 2.23 g of copper bronze (CAS number: 158113-12-3, copper-tin alloy comprising 90% by mass of copper and 10% by mass of tin, 12.2 mmol), 0.064 g of bipyridine (0.41 mmol) in 5 ml of DMSO were placed in a 50 ml three-necked round-bottomed flask equipped with a condenser, under a nitrogen atmosphere and with stirring. The resulting solution was heated to about 80° C. and 0.94 g of compound 3 (2.04 mmol) was then added. The temperature of the reaction medium was increased to about 130° C. and maintained for 5 hours. The reaction medium was cooled and poured into deionized water. The solution was then filtered through Celite®545 so as to give a clear filtrate. The solvents were evaporated off and the residue obtained was then extracted with ethyl acetate for 48 hours using a Soxhlet assembly. The organic phase was washed 3 times with aqueous 2M hydrochloric acid (HCl) solution, sodium bicarbonate solution and 3 times with deionized water. The resulting organic phase was dried over sodium sulfate and the solvents were evaporated off under vacuum. The residue obtained was dried under vacuum for 24 hours and then placed in a desiccator containing P2O5. The ionic monomer M$^3$ was obtained in a yield of about 70%.

The monomer M$^3$ was characterized by fluorine and proton NMR:

$^1$H NMR: δ (ppm, DMSO-d$_6$)=7.8 (d-d, 1H$_{Ar}$); 7.55 (d-d, 1H$_{Ar}$); 7.3 (d-d, 1H$_{Ar}$).

$^{19}$F NMR: δ (ppm, DMSO-d$_6$)=−118 (s, CF$_2$SO$_3$K); −111.5 (m, CF$_2$Ar); −108.4 (m, 1 F$_{Ar}$); −102.6 (m, 1 F$_{Ar}$); −87.5 (m, CF$_2$O); −82.3 (m, CF$_2$O).

Example 4

Preparation of a Difluoro Ionic Monomer M$^4$

The synthetic scheme for obtaining the difluoro ionic monomer M$^4$ is as follows:

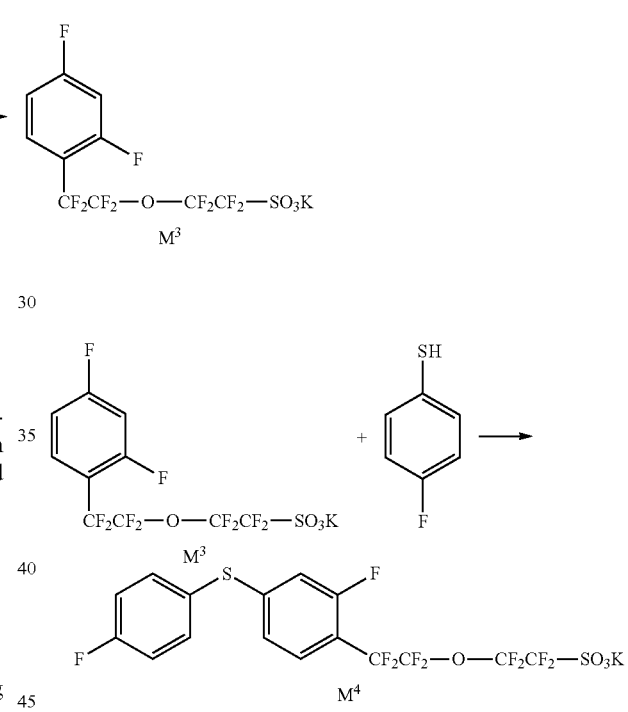

4.1) First Step: Synthesis of the Monomer M$^3$

The monomer M$^3$ was obtained according to the process as described in Example 3.

4.2) Second Step: Synthesis of Compound M$^4$ (3-{1,1,2,2-tetrafluoro-2-[1,1,2,2-tetrafluoro-2(potassiumoxysulfonyl)ethoxy]ethyl}-4,4'-difluoro-diphenylsulfide)

0.64 g of fluorothiophenol (4.9 mmol), 2 g of monomer M$^3$ (4.46 mmol) and 2.18 g of Cs$_2$CO$_3$ (6.69 mmol) in 8 ml of DMSO were placed in a 50 ml three-necked round-bottomed flask equipped with a condenser, under a nitrogen atmosphere and with stirring. The resulting solution was heated to about 65° C. for 16 hours and the resulting reaction medium was then diluted in water and extracted with ethyl acetate. The organic phase was washed with water and then dried over magnesium sulfate. The solvents were evaporated off under vacuum to give a residue. Said residue was purified by chromatography using a column of silica of $C_{18}$ type and a methanol/water eluent (55/45 v/v). The ionic monomer $M^4$ was obtained in a yield of about 65%.

The monomer $M^4$ was characterized by fluorine and proton NMR:

$^1$H NMR: δ (ppm, DMSO-$d_6$)=7.8 (d-d, 1$H_{Ar}$); 7.7-7.5 (m, 4$H_{Ar}$); 7.3 (d-d, 2$H_{Ar}$).

$^{19}$F NMR: δ (ppm, DMSO-$d_6$)=−118 (s, $CF_2SO_3K$); −112 (m, $CF_2Ar$); −113.4 (m, 1 $F_{Ar}$); −111.2 (m, 1 $F_{Ar}$); −87.5 (m, $CF_2O$); −82.3 (m, $CF_2O$).

Example 5

Preparation of a Difluoro Ionic Monomer $M^5$ in Accordance with the First Subject of the Invention The synthetic scheme for obtaining the difluoro ionic monomer $M^5$ is as follows:

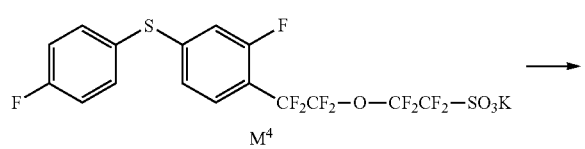

-continued

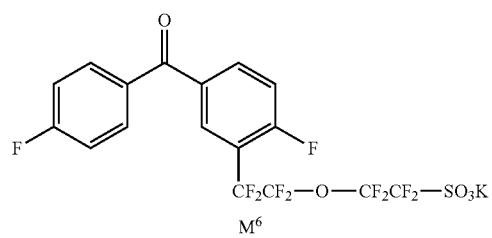

5.1) First Step: Synthesis of Monomer $M^4$

The monomer $M^4$ was obtained according to the process as described in Example 4.

5.2) Second Step: Synthesis of Compound $M^5$
(4-{1,1,2,2-tetrafluoro-2-[1,1,2,2-tetrafluoro-2(potassiumoxysulfonyl)ethoxy]ethyl}-3,4'-difluoro-diphenyl sulfone)

2 g of monomer $M^4$ (3.59 mmol) were placed in 78 ml of methanol in a round-bottomed flask. A solution comprising 4.42 g of oxone (potassium hydrogen persulfate, 7.18 mmol) in 4 ml of water was added to the resulting solution. The resulting reaction medium was stirred at room temperature for 5 hours. The reaction medium was then poured into aqueous 1M HCl solution and extracted with ethyl acetate. The organic phases were combined and washed with aqueous 1M HCl solution and saturated NaCl solution and then dried over sodium sulfate. The solvents were evaporated off under vacuum to give a residue. Said residue was purified by chromatography using a column of silica of $C_{18}$ type and a methanol/water eluent 55/45 v/v. The ionic monomer $M^5$ was obtained in a yield of about 60%.

The monomer $M^5$ was characterized by fluorine and proton NMR:

$^1$H NMR: δ (ppm, DMSO-$d_6$)=8.2 (m, 3$H_{Ar}$); 7.95 (s and d, 2$H_{Ar}$); 7.5 (d-d, 2$H_{Ar}$).

$^{19}$F NMR: δ (ppm, DMSO-$d_6$)=−118 (s, $CF_2SO_3K$); −111.3 (m, $CF_2Ar$); −108.7 (m, 1 $F_{Ar}$); −103.4 (m, 1 $F_{Ar}$); 86.9 (m, $CF_2O$); −82.2 (m, $CF_2O$).

Example 6

Preparation of a Difluoro Ionic Monomer $M^6$

The synthetic scheme for obtaining the difluoro ionic monomer $M^6$ is as follows:

6.1) First Step: Synthesis of Compound 3
(potassium 5-iodooctafluoro-3-oxapentanesulfonate)

Compound 3 was obtained by hydrolysis of 5-iodooctafluoro-3-pentanesulfonyl fluoride in an organic solvent in the presence of KOH according to the process as described in Example 1.1).

6.2) Second Step: Synthesis of Compound $M^6$
(3-{1,1,2,2-tetrafluoro-2-[1,1,2,2-tetrafluoro-2(potassiumoxysulfonyl)ethoxy]ethyl}-4,4'-difluoro-benzophenone)

6.5 g of 4,4'-difluoro-3-iodobenzophenone (18.89 mmol), 13.24 g of copper bronze (72.65 mmol) and 0.45 g of bipyridine (2.9 mmol) were placed in 30 ml of DMSO in a 250 ml three-necked round-bottomed flask equipped with a condenser, under a nitrogen atmosphere and with stirring. The resulting solution was heated to about 80° C., and 6.7 g of compound 3 (14.53 mmol) were then added. At the same time, the temperature of the reaction medium was increased to about 130° C. and maintained for 6 hours. The reaction medium was cooled and poured into deionized water. The solution was then filtered through Celite®545 so as to give a clear filtrate. The solvents were evaporated off and the residue obtained was then extracted with ethyl acetate for 48 hours using a Soxhlet assembly. The solvents were evaporated off under vacuum and the ionic monomer $M^6$ was obtained in a yield of about 70%.

The monomer $M^6$ was characterized by fluorine and proton NMR:

$^1$H NMR: δ (ppm, DMSO-d$_6$)=8.1 (m, 1H$_{Ar}$); 7.92 (d-d, 1H$_{Ar}$); 7.7 (2 d, 2H$_{Ar}$); 7.34 (d-d, 1H$_{Ar}$); 7.4 (2 d, 2H$_{Ar}$).
$^{19}$F NMR: δ (ppm, DMSO-d$_6$)=−118 (s, CF$_2$SO$_3$K); −112.4 (m, CF$_2$Ar); −107.2 (m, 1 F$_{Ar}$); −103.2 (m, 1 F$_{Ar}$); −87.5 (m, CF$_2$O); −82.3 (m, CF$_2$O).

Example 7

Preparation of Cation-Conducting Ionomers I$^1$ and I$^{1'}$ in Accordance with the Second Subject of the Invention The synthetic scheme for obtaining the ionomers I$^{1'}$ and I$^1$ is as follows:

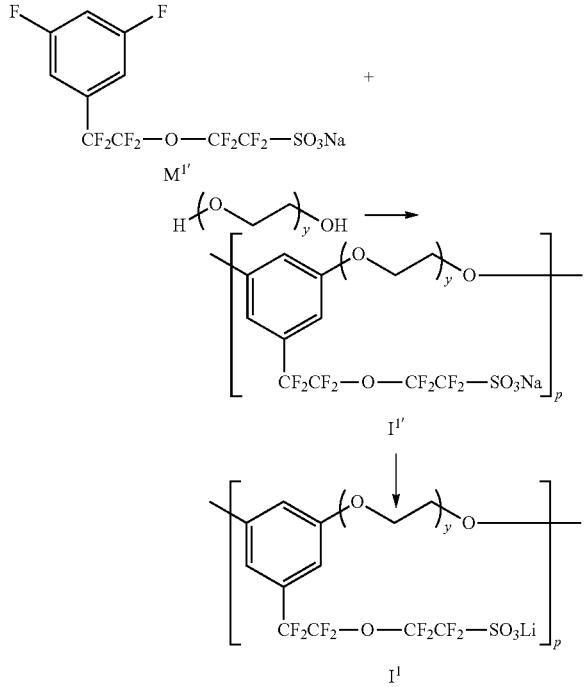

0.268 g of NaH (10.65 mmol, 2.3 equivalents) was placed in a three-necked round-bottomed flask under an argon atmosphere. A solution of 4.62 g of polyethylene glycol of molar mass 1000 g/mol (PEG 1000, y=22.7) (4.62 mmol, 1 equivalent) in 10 ml of diglyme was prepared in another flask. 2 to 3 ml of diglyme were then added to the flask containing the NaH and the resulting solution was added slowly to the solution containing the PEG 1000. The resultant reaction medium was heated at about 65° C. for 3 hours 30 minutes under an argon atmosphere.

In another flask, a solution containing 2 g of the monomer M$^{1'}$ sodium 3,5-(difluorophenyl)octafluoro-3-oxapentanesulfonate as prepared in Example 1 (4.62 mmol, 1 equivalent) in 5 ml of diglyme was prepared and the solution was added slowly to the reaction medium. The resulting reaction medium was heated at about 140° C. for 24 hours. It was then cooled to room temperature and precipitated from pentane to give a solid containing the ionomer I$^{1'}$. The solid was filtered off and then dissolved in acetonitrile. The solution obtained was filtered so as to remove the inorganic salts. The filtrate was evaporated on a rotavapor so as to obtain the ionomer in the form of a viscous liquid. This liquid was dried under vacuum at 100° C. for 48 hours.

Exchange of the sodium cation with the lithium cation was performed by ultrafiltration. The ionomer I$^{1'}$ was dissolved in aqueous 1M LiCl solution and then filtered under pressure with a membrane sold by the company Millipore under the commercial reference Ultracel® 3 kDa by the company Sodipro with a cutoff threshold of 1000 g/mol approximately (cellulose ultrafiltration membrane). The NaCl formed was also soluble in water, but passed through the membrane. When the solution became viscous, several aqueous 1M LiCl solutions were added so as to saturate the medium with lithium ions so as to better promote the exchange between the cations. Washing with water to remove a maximum amount of the NaCl formed was performed several times. This operation was performed for at least 24 hours and the resulting solution was then lyophilized. The residue obtained was dissolved in acetonitrile and filtered with filter paper and then with microfilters of about 0.2 μm so as to remove the excess LiCl and the remaining NaCl. The solvents were evaporated off under reduced pressure (10$^{-2}$ bar) and the ionomer I$^1$ obtained was dried under vacuum at about 60° C. for 24 hours (yield after drying of about 71%).

The ionomer I$^1$ was characterized by fluorine, carbon and proton NMR:

$^1$H NMR: δ (ppm, acétone-d$_6$)=6.92 (s, 2H, H$_3$); 6.74 (s, 1H, H$_1$); 4.25 (t, 4H, H$_9$, J=3.9 Hz); 3.84 (t, 4H, H$_{10}$, J=3.9 Hz); 3.62 (s, 90H, H$_{11}$, —O—(CH$_2$CH$_2$—O)—).
$^{13}$C NMR: δ (ppm, acetone-d$_6$)=162.1 (s, 2C, C$_2$); 132.5 (t, 1C, C$_4$, J=24.9 Hz); 107.3 (t, 2C, C$_3$, J=5.9 Hz); 107.1 (s, 1C, C$_1$); 113.9 (m, 1C, C$_6$); 119.4 (m, 1C, C$_8$); 122.1 (m, 1C, C$_7$); 116.7 (m, 1C, C$_5$); 73.0 (s, 2C, C$_9$); 71.8 (s, 45C, C$_{11}$, (CH$_2$CH$_2$—O)$_n$—); 69.9 (s, 2C, C$_{10}$).
$^{19}$F NMR: δ (ppm, acetone-d$_6$)=−83.37 (s, 2F, F$_6$); −88.08 (s, 2F, F$_7$); −113.88 (s, 2F, F$_5$); −118.80 (s, 2F, F$_8$).

The number-average molar mass M$_n$ of the ionomer I$_1$ was 21 000 g/mol approximately and its mass-average molar mass M$_2$ was 36 700 g/mol approximately.

The ionomer I$_1$ had a value p of about 15 and a value y of about 22.7.

Example 8

Preparation of Cation-Conducting Ionomers I$^{2'}$; I$^2$, I$^{3'}$ and I$^3$ in Accordance with the Second Subject of the Invention The synthetic scheme for obtaining the ionomers I$^{2'}$; I$^2$, I$^{3'}$ and I$^3$ is as follows:

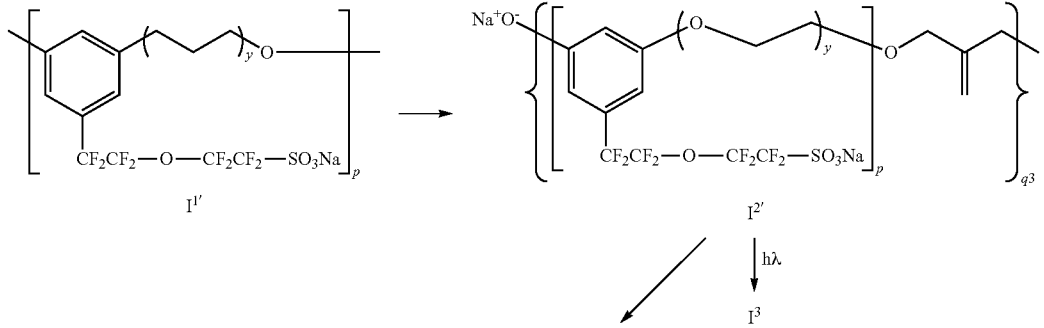

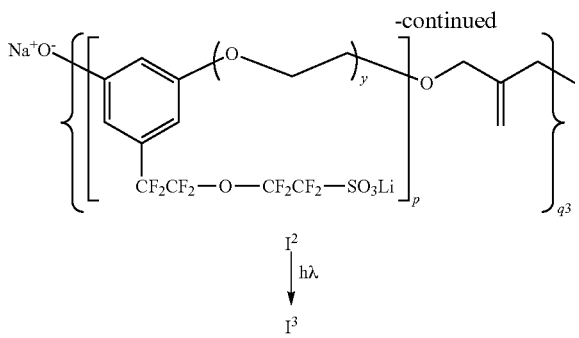

0.315 g of NaH (12.5 mmol, 2.7 equivalents) was placed in a three-necked round-bottomed flask under an argon atmosphere. A solution of 5.32 g of polyethylene glycol of molar mass 1000 g/mol (PEG 1000, n=22.7) (5.32 mmol, 1.15 equivalents) in 6 ml of diglyme was prepared in another flask. 2 to 3 ml of diglyme were then added to the flask containing the NaH and the resulting solution was added slowly to the solution containing the PEG 1000. The resulting reaction medium was heated at about 65° C. for 3 hours 30 minutes under an argon atmosphere.

A solution containing 2 g of the monomer $M^{1'}$ sodium 3,5-(difluorophenyl)octafluoro-3-oxapentanesulfonate as prepared in Example 1 (4.62 mmol, 1 equivalent) in 3 ml of diglyme was prepared in another flask and the solution was added slowly to the reaction medium. The resulting reaction medium was heated at about 140° C. for 24 hours. It was then cooled to about 60° C. and 7.18 mmol of ground NaOH were added. The resulting reaction medium was stirred for about 2 hours.

Next, 0.7 mmol of 3-chloro-2-chloroprop-1-ene was added and the resulting reaction medium was stirred for about 12 hours. The solid was filtered off and then dissolved in acetonitrile. The solution obtained was filtered so as to remove the inorganic salts. The filtrate was evaporated on a rotavapor so as to obtain the ionomer in the form of a viscous liquid. This liquid was dried under vacuum at 100° C. for 48 hours (yield of ionomer $I^{2'}$ of about 79%).

The number-average molar mass $M_n$ of the ionomer $I^{1'}$ obtained was about 7600 g/mol and its mass-average molar mass $M_w$ was about 13 100 g/mol.

The ionomer $I^{1'}$ had a value p of about 5.5 and a value y of about 22.7.

The ionomer $I^{2'}$ was characterized by fluorine, carbon and proton

NMR:

$^1$H NMR: δ (ppm, acetone-d$_6$)=6.92 (s, 2H, H$_3$); 6.74 (s, 1H, H$_1$); 5.16 (s, 2H, H$_{14}$); 4.26 (s, 4H, H$_9$); 4.00 (s, 4H, H$_{12}$); 3.84 (s, 4H, H$_{10}$); 3.62 (s, 90H, H$_{11}$, —O—(CH$_2$CH$_2$—O)—).

$^{13}$C NMR: δ (ppm, acetone-d$_6$)=162.1 (s, 1C, C$_2$); 145.5 (s, 1C, C$_{13}$); 132.5 (t, 1C, C$_4$, J=24.9 Hz); 107.3 (t, 2C, C$_3$, J=5.9 Hz); 107.1 (s, 1C, C$_1$); 113.9 (m, 1C, C$_6$); 119.4 (m, 1C, C$_8$); 122.1 (m, 1C, C$_7$); 116.7 (m, 1C, C$_5$); 73.0 (s, 4C, C$_9$); 71.8 (s, 45C, C$_{11}$, (CH$_2$CH$_2$—O)$_n$—); 71.1 (s, 4C, C$_{12}$); 69.9 (s, 4C, C$_{10}$).

$^{19}$F NMR: δ (ppm, acetone-d$_6$)=−83.28 (s, 2F, F$_6$); −87.95 (s, 2F, F$_7$); −113.58 (s, 2F, F$_5$); −118.68 (s, 2F, F$_8$).

The ionomer $I^2$ (in lithiated form) was obtained by cation exchange of the ionomer $I^{2'}$ according to the following ultrafiltration protocol:

The ionomer $I^{2'}$ was dissolved in aqueous 1M LiCl solution and then filtered under pressure with a cellulose ultrafiltration membrane having a cutoff threshold of about 1000 g/mol as defined in Example 7. The NaCl formed was also soluble in water, but passed through the membrane. When the solution became viscous, several aqueous 1M LiCl solutions were added so as to saturate the medium with lithium ions so as to better promote the exchange between the cations. Washing with water in order to remove a maximum amount of NaCl formed was performed several times. This operation was performed for at least 24 hours and the resulting solution was then lyophilized. The residue obtained was dissolved in acetonitrile and filtered with a paper filter and then with microfilters of about 0.2 μm so as to remove the excess LiCl and the remaining NaCl. The solvents were evaporated off under reduced pressure (10$^{-2}$ bar) and the ionomer $I^2$ obtained was dried under vacuum at about 60° C. for 24 hours (yield of ionomer $I^2$ of about 79%).

The number-average molar mass $M_n$ of the ionomer $I^2$ was about 22 100 g/mol and its mass-average molar mass $M_w$ was about 38 100 g/mol.

The ionomer $I^2$ had a value y of about 22, a value p of about 5.5 and a value q$_3$ of about 3.

The ionomers $I^{2'}$ and $I^2$ were then crosslinked according to the following protocol:

1 g of ionomer $I^{2'}$ or $I^2$ was dissolved in 10 ml of acetonitrile containing 0.02 g of Irgacure®2959. The resulting solution was stirred in the absence of light for about 2 hours. The solution was then degassed and poured into a Petri dish. The solvent was evaporated off at room temperature. The ionomer was then crosslinked by two irradiations lasting 30 seconds each, with an interval of one minute between the two irradiations, using a UV lamp. The crosslinked ionomer $I^{3'}$ or $I^3$ obtained was dried under vacuum at about 70° C. for at least 72 hours and stored in a glovebox.

Example 9

Preparation of a Cation-Conducting Ionomer $I^{4'}$ in Accordance with the Second Subject of the Invention The synthetic scheme for obtaining the ionomer $I^{4'}$ is as follows:

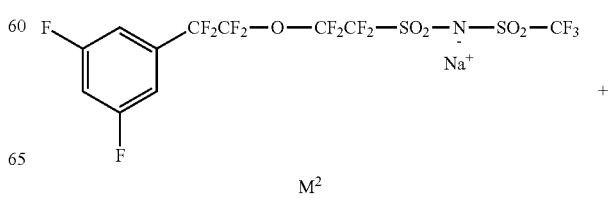

-continued

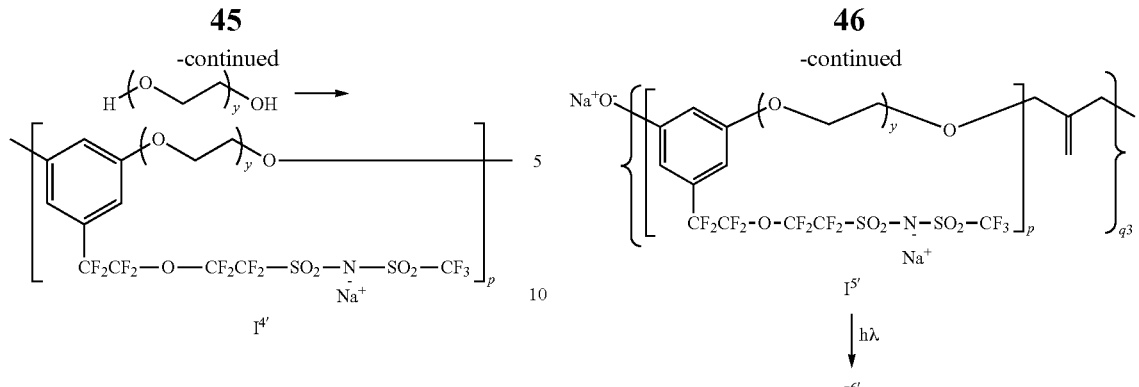

0.075 g of NaH (2.45 mmol, 2.3 equivalents) was placed in a three-necked round-bottomed flask under an argon atmosphere. A solution of 1.285 g of polyethylene glycol of molar mass 1000 g/mol (PEG 1000, n=22.7) (1.285 mmol, 1 equivalent) in 4 ml of diglyme was prepared in another flask. 3 ml of diglyme were then added to the flask containing the NaH and the resulting solution was added slowly to the solution containing the PEG 1000. The resulting reaction medium was heated at about 65° C. for 3 hours 30 minutes under an argon atmosphere.

A solution containing 0.725 g of the monomer $M^2$ as prepared in Example 2 (1.287 mmol, 1 equivalent) in 3 ml of diglyme was prepared in another flask and the solution was added slowly to the reaction medium. The resulting reaction medium was heated at about 140° C. for 24 hours. It was then cooled to room temperature and precipitated from pentane to give a solid containing the ionomer $I^{4'}$. The solid was filtered off and then dissolved in acetonitrile. The solution obtained was filtered so as to remove the inorganic salts. The filtrate was evaporated from a rotavapor so as to obtain the ionomer $I^{4'}$ in the form of a viscous liquid. This liquid was dried under vacuum at 100° C. for 48 hours (yield of ionomer $I^{4'}$ of about 62%).

The ionomer $I^{4'}$ was characterized by fluorine and proton NMR:

$^1$H NMR: δ (ppm, acetone-$d_6$)=6.83 (s, 2H, $H_3$); 6.79 (s, 1H, $H_1$); 4.21 (t, 4H, $H_{10}$); 3.83 (t, 4H, $H_{11}$); 3.60 (s, 90H, $H_{12}$, —O—($CH_2CH_2$—O)—).

$^{19}$F NMR: δ (ppm, acetone-$d_6$)=−79.65 (s, 3F, $F_9$); −82.05 (s, 2F, $F_6$); −87.74 (s, 2F, $F_7$); −113.85 (s, 2F, $F_5$); −117.20 (s, 2F, $F_8$).

Example 10

Preparation of Cation-Conducting Ionomers $I^{5'}$ and $I^{6'}$ in Accordance with the Second Subject of the Invention The synthetic scheme for obtaining the ionomers $I^{5'}$ and $I^{6'}$ is as follows:

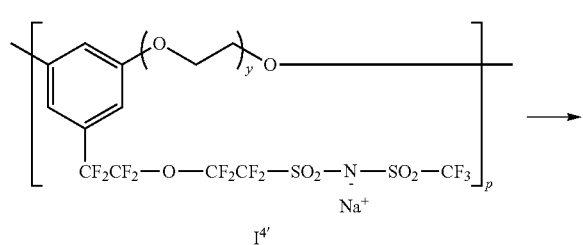

0.075 g of NaH (2.45 mmol, 2.3 equivalents) was placed in a three-necked round-bottom flask under an argon atmosphere. A solution of 1.285 g of polyethylene glycol of molar mass 1000 g/mol (PEG 1000, n=22.7) (1.285 mmol, 1 equivalent) in 4 ml of diglyme was prepared in another flask. 3 ml of diglyme were then added to the flask containing the NaH and the resulting solution was added slowly to the solution containing the PEG 1000. The resulting reaction medium was heated at about 65° C. for 3 hours 30 minutes under an argon atmosphere.

A solution containing 0.725 g of the monomer $M^2$ as prepared in Example 2 (1.287 mmol, 1 equivalent) in 3 ml of diglyme was prepared in another flask and the solution was added slowly to the reaction medium. The resulting reaction medium was heated at about 140° C. for 24 hours.

The reaction medium was cooled to about 60° C. and 1 mmol of ground NaOH was added. The resulting reaction medium was stirred for about 2 hours. 0.213 mmol of 3-chloro-2-chloroprop-1-ene was then added and the resulting reaction medium was stirred for about 12 hours. The solid was filtered off and then dissolved in acetonitrile. The solution obtained was filtered so as to remove the inorganic salts. The filtrate was evaporated on a rotavapor so as to obtain the ionomer in the form of a viscous liquid. This liquid was dried under vacuum at 100° C. for 48 hours (yield of ionomer $I^{5'}$ of about 88%).

The ionomer $I^{5'}$ was characterized by fluorine and proton NMR:

$^1$H NMR: δ (ppm, acétone-$d_6$)=6.82 (s, 2H, $H_3$); 6.76 (s, 1H, $H_1$); 5.16 (s, 2H, $H_{15}$); 4.23 (s, 4H, $H_{10}$); 4.00 (s, 4H, $H_{13}$); 3.83 (s, 4H, $H_{11}$); 3.60 (s, 90H, $H_{12}$, —O—($CH_2CH_2$—O)—).

$^{19}$F NMR: δ (ppm, acetone-$d_6$)=−79.77 (s, 3F, $F_9$); −82.14 (s, 2F, $F_6$); −87.78 (s, 2F, $F_7$); −113.93 (s, 2F, $F_5$); −117.30 (s, 2F, $F_8$).

The ionomer $I^{5'}$ was then crosslinked according to the protocol of Example 8.

Example 11

Preparation of Electrolytic Compositions in Accordance with the Third Subject of the Invention Several electrolytic compositions were analysed by differential scanning calorimetry:

an electrolytic composition $C^{3'}$ constituted of the ionomer $I^{3'}$ of Example 8, an electrolytic composition $C^3$ constituted of the ionomer $I^3$ of Example 8, and an electrolytic composition $C^{3'}$-A constituted of 90% by mass of the ionomer $I^{4'}$ of Example 8 and 10% by mass of cellulose nanofibres functionalized with sodium sulfonate groups $Na^+$—$SO_3^-$ (NCC).

The NCCs were provided by the company FP Innovation, Canada. They are obtained from hardwood.

The electrolytic composition C³'-A was prepared in the following manner:

4 g of NCC were dispersed in 100 ml of distilled water in a container. The resulting dispersion was subjected to 4 cycles of 5 minutes of homogenization using a disperser, by imposing a speed of 13 000 rpm, especially with a machine sold under the trade name IKA® Ultra-Turrax. The resulting dispersion was then subjected to ultrasonication using an ultrasound probe sold under the trade name VCX130 by the company Sonics & Materials, Inc., dipped directly into the dispersion. The duration of the ultrasonication cycle was about 15 minutes, with a pulse whose intensity was 6 out of 9. The container containing the dispersion was placed in a cold bath to prevent heating of said dispersion. Typically, to achieve homogeneous dispersion, about ten ultrasonication cycles were necessary for the NCCs used.

0.9 g of ionomer $I^{2'}$ was dissolved in 10 ml of water containing 0.02 g of Irgacure® 2959. 2.5 ml (i.e. 0.1 g of NCC) of the dispersion of NCC in water as prepared previously were added to the resulting solution. The resulting dispersion was stirred in the absence of light for about 2 hours. The dispersion was then degassed and poured into a Petri dish. The solvent was evaporated off at room temperature. The ionomer was then crosslinked by two irradiations lasting 30 seconds each, with an interval of one minute between the two irradiations, using a UV lamp. The electrolytic composition C³'-A obtained was dried under vacuum at about 70° C. for at least 72 hours and stored in a glovebox.

The DSC analyses are given in FIG. 1 (heat flow as a function of the temperature) and showed that the ionomers of compositions C³ (curve with the crosses), C³' (curve with the triangles) and C³'-A (curve with the circles) were entirely amorphous since no melting peak was observed. Moreover, the glass transition temperatures $T_g$ of said ionomers were of the same order of magnitude as those obtained with an electrolyte of the prior art POE/LiTFSI (i.e. about −34 to −40° C.).

Figure 2:
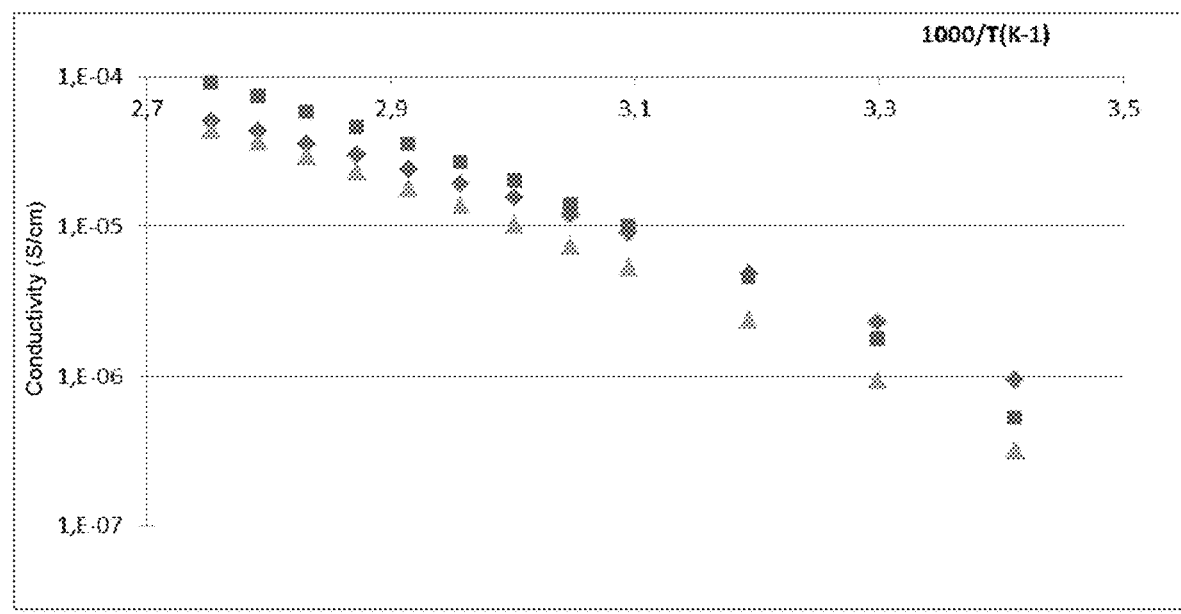
FIG. 2 is an Ion conductivity test between 20 and 90° C. from example 11, in accordance with one embodiment

Ion conductivity tests between 20 and 90° C. are reported in FIG. 2 and showed that at 50° C., the conductivity of composition C³ (filled diamonds) and of composition C³' (filled squares) was about $1 \times 10^{-5}$ S·cm⁻¹. That of composition C³'-A (filled triangles) was slightly smaller, but the mechanical stability of said composition C³'-A was improved due to the presence of the functionalized cellulose nanofibres NCC.

The NCCs also make it possible to reduce the dendritic growth.

Figure 3:
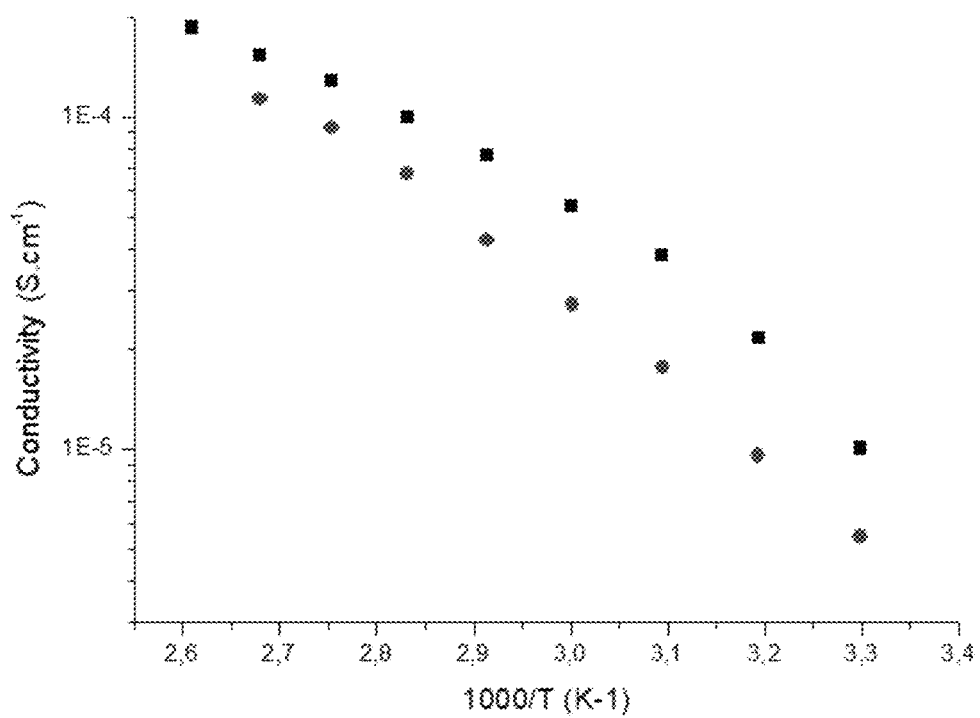
FIG. 3 is an ion conductivity test between 20 and 90° C. performed on electrolytic compositions from example 11, in accordance with one embodiment.

Tests of ion conductivity between 20 and 90° C. were also performed on electrolytic compositions C¹' and C⁴', respectively constituted of the ionomer I¹' and the ionomer I⁴', and are reported in FIG. 3.

They showed that at 50° C., the conductivity of C⁴' (filled squares) is $4 \times 10^{-5}$ S·cm⁻¹ and that of C¹' (filled circles) is $1.8 \times 10^{-5}$ S·cm⁻¹.

Moreover, the ion transport numbers of the crosslinked ionomers I³, I³', I⁶ (i.e. of formula similar to that of I⁶' but in the lithium form instead of the sodium form) and I⁶' were 1.

The invention claimed is:

1. Process for preparing an ionomer comprising at least repeating units UP corresponding to formula (II) below:

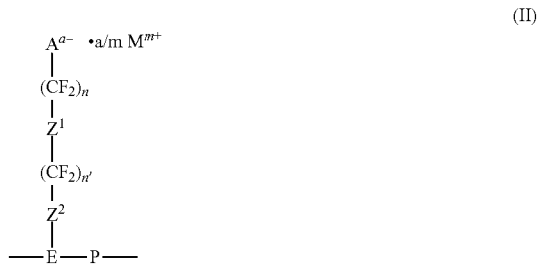

in which

M is an alkali metal cation, an alkaline-earth metal cation, a transition metal cation, a poor metal cation, an ammonium, a sulfonium or a phosphonium of valency m, with $1 \leq m \leq 3$, m being an integer, $A^{a-}$ is an anion chosen from a sulfonate anion, a sulfonimide anion of formula —SO₂—N⁻—SO₂R, an anion derived from a sulfonimide anion bearing at least two negative charges, and a carbanion of formula —SO₂—C⁻R'R", with $1 \leq a \leq 3$, a being an integer, with R representing a fluorine atom; an optionally fluoro or perfluoro alkyl group, containing from 1 to 10 carbon atoms; an optionally fluoro or perfluoro alkoxy group, containing from 1 to 10 carbon atoms; a phenoxy group optionally substituted with an electron-withdrawing group $X^2$; an optionally fluoro or perfluoro dialkyl ether group, containing from 1 to 10 carbon atoms; a thiocyanate group; an optionally substituted phenyl group; a nitrile group; an amino group of formula —NR¹R², in which R¹ and R² are chosen, independently of each other, from the following groups: an optionally fluoro or perfluoro alkyl group, containing from 1 to 5 carbon atoms, an alkyl group containing from 1 to 5 carbon atoms and bearing an electron-withdrawing group $X^3$, an optionally fluoro or perfluoro dialkyl ether group, containing from 1 to 5 carbon atoms, and an electron-withdrawing group $X^4$; a group —NR³ being chosen from a saturated heterocycle containing from 3 to 6 carbon atoms and an unsaturated heterocycle containing from 4 to 6 carbon atoms; an amide group of formula —NH—CO—R⁴ or —N(CH₃)—CO—R⁴, in which R⁴ is an alkyl group containing from 1 to 3 carbon atoms; a sulfonamide group of formula —NH—SO₂—R⁵ or —N(CH₃)—SO₂—R⁵, in which R⁵ is an alkyl group containing from 1 to 3 carbon atoms; a urethane group of formula —NH—CO₂—R⁶ or —N(CH₃)—CO₂—R⁶, in which R⁶ is an alkyl group containing from 1 to 3 carbon atoms; a cyanamide group of formula NH—CN or N(R⁷)—CN, in which R⁷ is an alkyl group containing 1 to 3 carbon atoms; a dicyanamide group —N(CN)₂; a tricyanomethyl group —C(CN)₃; or a dicyanomethylene group of formula —CH(CN)₂ or —CR⁸(CN)₂, in which R⁹ is an alkyl group containing 1 to 3 carbon atoms, with R' and R" being chosen, independently of each other, from the following monovalent groups: a fluorine atom; a thiocyanate group; a nitrile group; a nitro group; a nitroso group of formula R⁹NO—, in which R⁹ is an alkyl group containing from 1 to 3 carbon atoms; a carbonyl group of formula —COR¹⁰ in which R¹⁰ is a perfluoro alkyl group containing from 1 to 5 carbon atoms; a sulfoxide group of formula —SOR¹¹ in which R¹¹ is an optionally fluoro or perfluoro alkyl group, containing from 1 to 5 carbon atoms or an optionally fluoro or perfluoro dialkyl ether group, containing from 1 to 5 carbon atoms; a sulfonyl group of formula —SO$_2$R$^{12}$ in which R$^{12}$ is a fluorine atom, a thiocyanate group, a nitrile group, an optionally fluoro or perfluoro alkoxy group, containing from 1 to 5 carbon atoms, an optionally fluoro or perfluoro alkyl group, containing from 1 to 5 carbon atoms or an optionally fluoro or perfluoro dialkyl ether group, containing from 1 to 5 carbon atoms; a carboxylic ester group of formula —COOR$^{13}$, in which R$^{13}$ is an alkyl group containing from 1 to 5 carbon atoms; an amide group of formula —CONHR$^{14}$ in which R$^{14}$ is an alkyl group containing from 1 to 5 carbon atoms; an amide group of formula —CONR$^{14}$R$^{15}$ in which R$^{14}$ and R$^{15}$ are chosen, independently of each other, and R$^{15}$ is an alkyl group containing from 1 to 5 carbon atoms; an optionally substituted phenyl group; or an optionally substituted phenoxy group, or with R' and R'' being divalent groups such that the resulting carbanion radical —C$^-$R'R'' forms an aromatic ring comprising from 5 to 6 carbon atoms and optionally one or more heteroatoms O or N, said aromatic ring being optionally substituted with one or more nitrile groups, 1≤n≤4, n being an integer, 0≤n'≤2, n' being an integer, Z$^1$ is chosen from a single bond, an oxygen atom, a sulfur atom, a group —S=O, a group —S(=O)$_2$ and a phenyl group optionally substituted in the ortho position relative to one of the functions (CF$_2$)$_n$ or (CF$_2$)$_{n'}$, Z$^2$ is chosen from a single bond, an oxygen atom, a sulfur atom, a group —S=O, a group —S(=O)$_2$ and a group —C=O, it being understood that when n'=0, Z$^2$ is a single bond, E is an aromatic group comprising from 5 to 20 carbon atoms, it being understood that E comprises from 1 to 3 aromatic rings, and P is an alkylene oxide polymer chain, wherein said process comprises at least one step a) of polycondensation of at least one difluoro ionic monomer (I) with at least one alkylene oxide polymer P$^1$ in basic medium, said difluoro ionic monomer corresponding to formula (I) below:

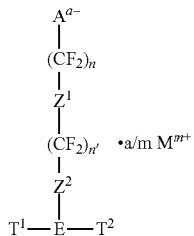

(I)

in which:

A, n, n', Z$^1$, Z$^2$, E, m, a and M are as defined above, and T$^1$ and T$^2$ are fluorine atoms.

2. Process according to claim 1, wherein the alkylene oxide polymer P$^1$ used in step a) is chosen from the polymers having the following formulae:

in which 2≤x≤4, 1≤y≤50,

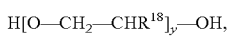

in which R$^{18}$ is an alkyl group containing from 1 to 8 carbon atoms or an alkoxy group containing from 1 to 8 carbon atoms, and 1≤y≤50,

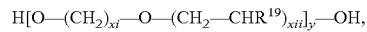

in which 1≤xi≤4; 1≤xii≤2; R$^{19}$ is a hydrogen atom or an alkyl group containing from 1 to 8 carbon atoms; 1≤y≤50,

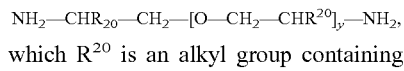

in which R$^{20}$ is an alkyl group containing from 1 to 8 carbon atoms; and 1≤y≤50, and

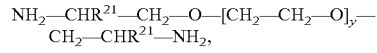

in which R$^{21}$ is an alkyl group containing from 1 to 8 carbon atoms; and 1≤y≤50.

3. Process according to claim 1 wherein said process also comprises, after step a), at least one step b) of placing the ionomer in contact with a compound G comprising at least two functions F$^1$ that are capable of polycondensing with said ionomer and optionally at least one post-polymerizable function F$^2$.

4. Process according to claim 3, wherein compound G comprises a post-polymerizable function F$^2$ and the process also comprises a step c) of post-polymerization of the ionomer obtained on conclusion of step b).

5. Process according to claim 1 wherein said process also comprises, after step a), at least one step d) of placing the ionomer in contact with a compound H comprising a function F$^1$ that is capable of condensing with said ionomer and optionally at least one post-polymerizable function F$^2$.

6. Process according to claim 1 wherein said process also comprises, after step a), at least one step f) of placing the ionomer in contact with a compound J that is capable of reacting with said ionomer according to a radical or ionic polymerization.

7. Process according to claim 1, wherein the difluoro ionic monomer (I) is prepared according to a process comprising at least one step i) of reacting a compound (I-a) with a compound (I-b) according to the following reaction scheme:

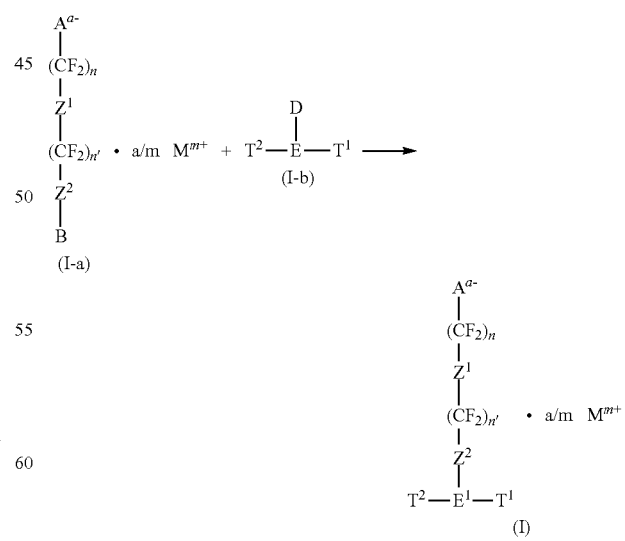

or at least one step i') of reacting a compound (I'-a) with a compound (I'-b) according to the following reaction scheme:

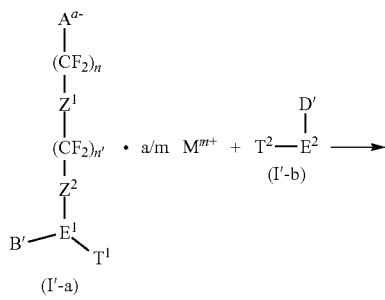
(I'-a)

or at least one step i") of reacting a compound (I"-a) with a compound (I"-b) according to the following reaction scheme:

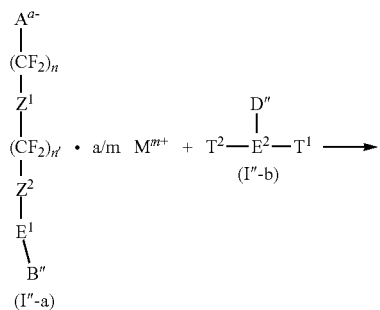

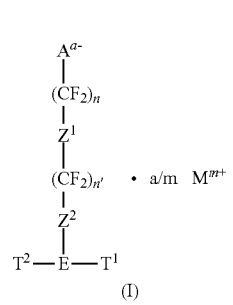

with $Z^1$, $Z^2$, n, n', $T^1$, $T^2$, E, A, a, m and M being as defined in the invention, and the groups B and D, the groups B' and D' and the groups B" and D" being chosen appropriately so as to be able to react together and $E^1$ and $E^2$ being chosen appropriately so as to be able to form the aromatic group E.

8. Process according to claim 1, wherein the difluoro ionic monomer (I) corresponds to any one of the following formulae:

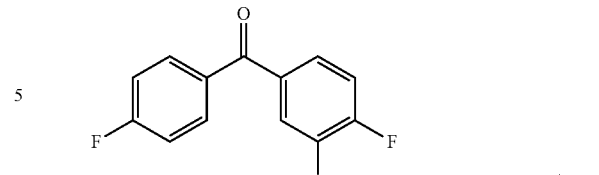

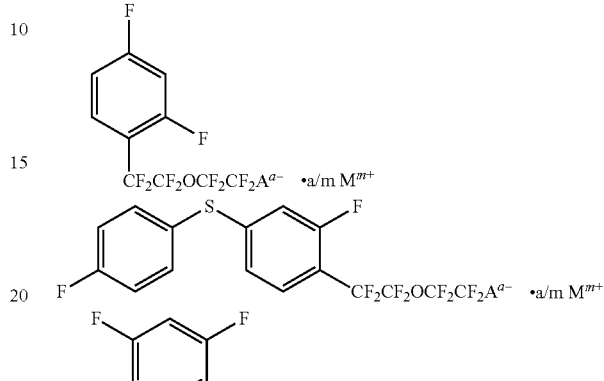

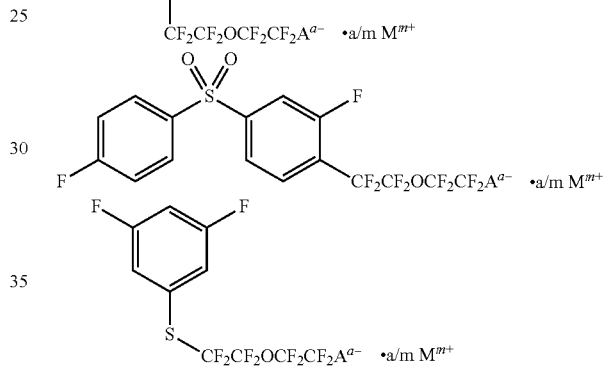

in which M, A, a and m are as defined in claim 1.

9. Ionomer, obtained according to the process as defined in claim 1, said ionomer comprises at least repeating units UP corresponding to formula (II) below:

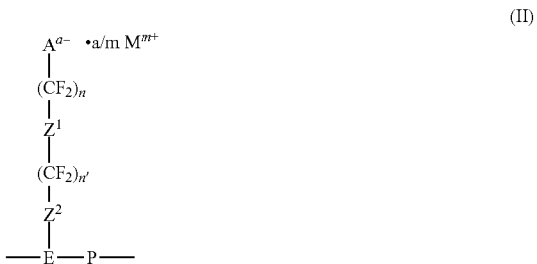

(II)

in which A, n, n', $Z^1$, $Z^2$, E, m, a and M are as defined in claim 1, and P is an alkylene oxide polymer chain.

10. Ionomer according to claim 9, wherein the alkylene oxide polymer chain corresponds to any one of the following formulae:

—[O—(CH$_2$)$_x$]$_y$—O—, in which 2≤x≤4, 1≤y≤50,

[O—CH$_2$—CHR$^{18}$]$_y$—O—, in which $R^{18}$ is an alkyl group containing from 1 to 8 carbon atoms or an alkoxy group containing from 1 to 8 carbon atoms, and $1 \leq y \leq 50$,

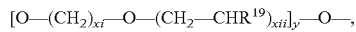

in which $1 \leq xi \leq 4$; $1 \leq xii \leq 2$; $R^{19}$ is a hydrogen atom or an alkyl group containing from 1 to 8 carbon atoms; $1 \leq y \leq 50$,

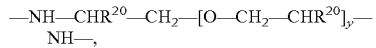

in which $R^{20}$ is an alkyl group containing from 1 to 8 carbon atoms; and $1 \leq y \leq 50$, or

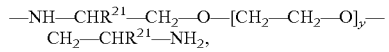

in which $R^{21}$ is an alkyl group containing from 1 to 8 carbon atoms; and $1 \leq y \leq 50$.

11. Ionomer according to claim 9, wherein the aromatic group E comprises from 5 to 15 carbon atoms.

12. Ionomer according to claim 9, wherein the aromatic group E is chosen from a phenyl group, a benzophenone group, a diphenyl sulfide group and a diphenyl sulfone group.

13. Ionomer according to claim 9, wherein M is a cation of an alkali metal or a cation of an alkaline-earth metal.

14. Ionomer according to claim 9, wherein one or more of the following conditions apply:
n=n'=2,
$Z^1$ is an oxygen atom,
$Z^2$ is a sulfur atom or a single bond.

15. An ionic liquid comprising:
an ionomer obtained according to the process as defined in claim 1.

16. A constituent of a composite comprising:
an ionomer obtained according to the process as defined in claim 1.

17. An electrochemical device comprising:
an electrolyte manufactured with an ionomer obtained according to the process as defined in claim 1.

18. Electrolytic composition, wherein said electrolytic composition comprises at least one ionomer obtained according to the process as defined in claim 1.

19. Electrolytic composition according to claim 18, wherein said electrolytic composition also comprises one or more organic solvents.

20. Electrolytic composition according to claim 18, wherein said electrolytic composition also comprises one or more additives chosen from mineral fillers, alkali metal salts, organic fillers, complexing agents, flame retardants, and a mixture thereof.

21. Electrolytic composition according to claim 18, wherein said electrolytic composition is constituted solely of said ionomer.

22. Electrochemical device comprising;
at least one negative electrode and at least one positive electrode separated by an electrolytic composition, wherein the electrolytic composition is as defined in claim 18.

* * * * *